United States Patent
Shibasaki et al.

(10) Patent No.: US 7,233,872 B2
(45) Date of Patent: Jun. 19, 2007

(54) DIFFERENCE CORRECTING METHOD FOR POSTURE DETERMINING INSTRUMENT AND MOTION MEASURING INSTRUMENT

(75) Inventors: Ryosuke Shibasaki, Tokyo (JP); Yusuke Konishi, Tokyo (JP); Hiroshi Kanasugi, Tokyo (JP); Nobuyuki Yoshida, Tokyo (JP)

(73) Assignee: Akebono Brake Industry Co., Ltd., Tokyo (JP)

( * ) Notice: Subject to any disclaimer, the term of this patent is extended or adjusted under 35 U.S.C. 154(b) by 0 days.

(21) Appl. No.: 10/545,388

(22) PCT Filed: Feb. 16, 2004

(86) PCT No.: PCT/JP2004/001611

§ 371 (c)(1),
(2), (4) Date: Aug. 12, 2005

(87) PCT Pub. No.: WO2004/072579

PCT Pub. Date: Aug. 26, 2004

(65) Prior Publication Data

US 2006/0161363 A1    Jul. 20, 2006

(30) Foreign Application Priority Data

Feb. 14, 2003    (JP) .............................. 2003-037054

(51) Int. Cl.
*G01C 17/38*    (2006.01)
*G01P 21/00*    (2006.01)
*G06F 19/00*    (2006.01)

(52) U.S. Cl. ...................... 702/94; 702/95; 702/150; 702/151; 702/152; 702/153; 33/512

(58) Field of Classification Search ................. 702/94, 702/95

See application file for complete search history.

(56) References Cited

FOREIGN PATENT DOCUMENTS

| JP | 9-229667 A | 9/1997 |
|----|------------|--------|
| JP | 9-318382 A | 12/1997 |
| JP | 11-325881 A | 11/1999 |
| JP | 2000-321044 A | 11/2000 |
| JP | 2000-356520 A | 12/2000 |

*Primary Examiner*—John Barlow
*Assistant Examiner*—Sujoy Kundu
(74) *Attorney, Agent, or Firm*—Knobbe, Martens, Olson & Bear LLP

(57) ABSTRACT

The error of a sensor in motion capture system is corrected. An acceleration sensor determines the direction of gravity (G1) in a still initial state. The direction G1 will never change always if a drift dose not occur. However, actually if an object to which an acceleration sensor is attached moves along a coordinate axis, the direction gradually changes due to a drift with time. According to the invention, after a given time has passed, the acceleration sensor is stopped to determine the direction of gravity. Referring to the data on this determination, the true direction of gravity to be judged is compared with the direction of gravity G1 influenced by the drift. The difference between them is assumed to be an error due to a drift, and the error is subtracted from the determined value to correct the error of the measurement value. Similarly to the direction of gravity, assuming that there is an error in any direction in the coordinate system, the errors are corrected, and more accurate motion determination is possible.

6 Claims, 17 Drawing Sheets

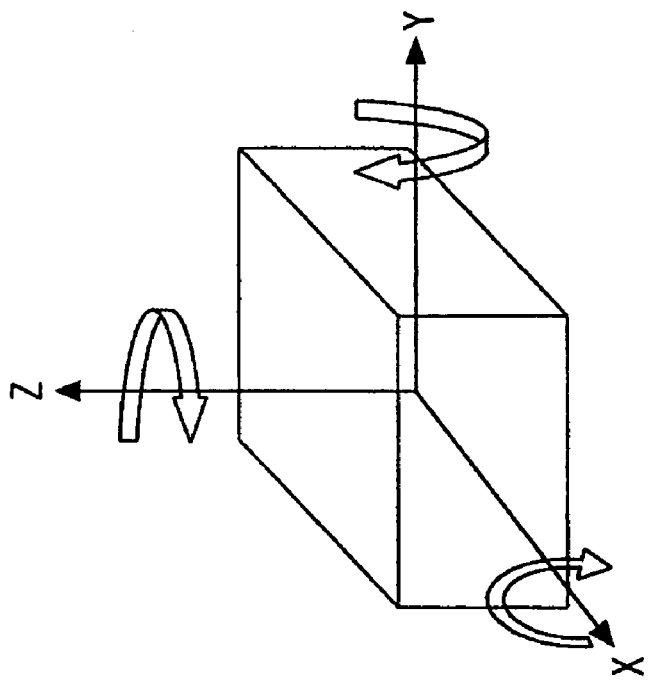
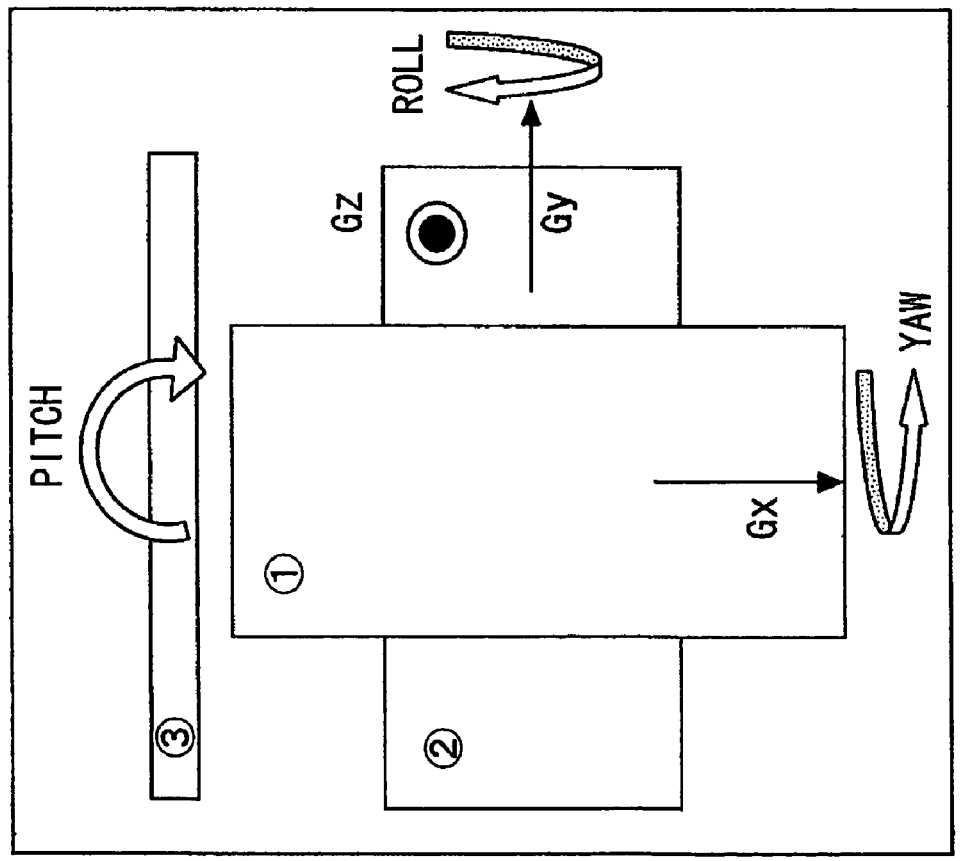
FIG. 4

FIG. 12
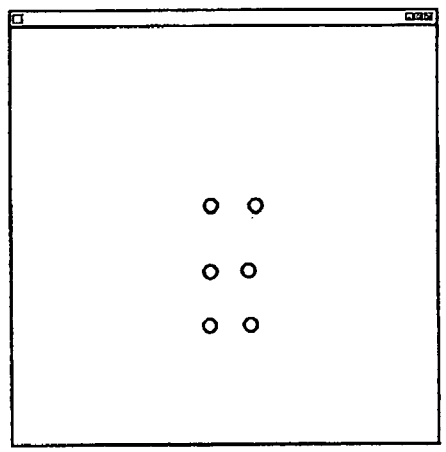
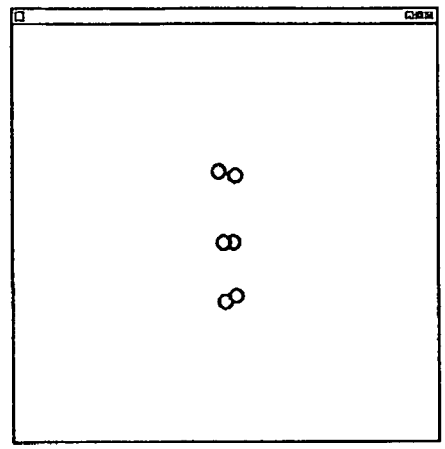
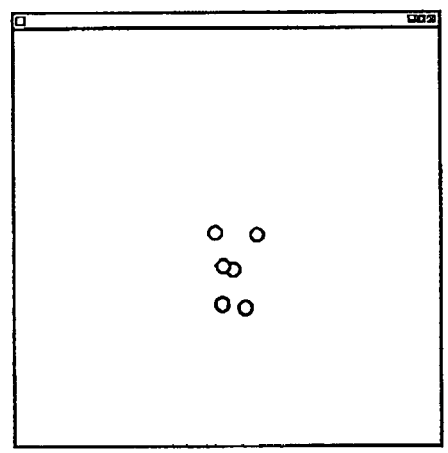
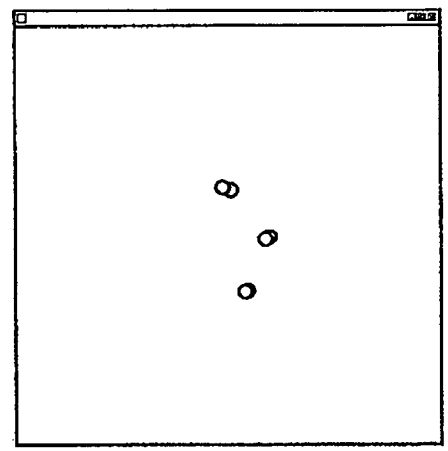
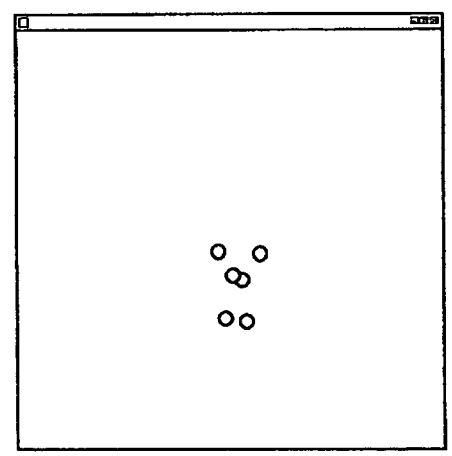
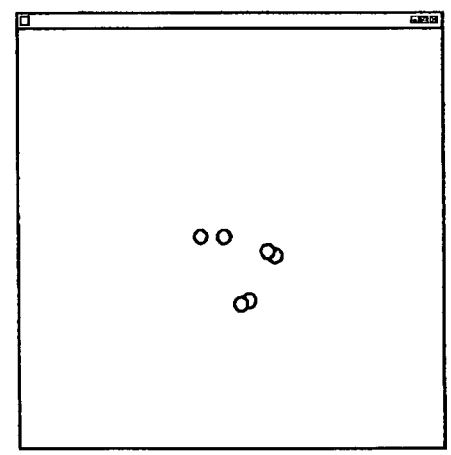
FRONT SIDE

DIFFERENCE CORRECTING METHOD FOR POSTURE DETERMINING INSTRUMENT AND MOTION MEASURING INSTRUMENT

TECHNICAL FIELD

The present invention relates to a so-called motion capture system which measures an operation of a target based on data from a sensor attached to a human or another moving object, and further to an operation determining instrument used for the system, in particular, an instrument having a feature in a correcting method of its determination data.

BACKGROUND ART

Conventional technologies for measuring motions of human bodies or the like are classified into a method of installing a sensor in a place away from a measuring target to measure it (method by remote measurement), and a method of attaching a sensor to a measuring target itself to measure its motion without relying on a signal or the like from the outside (method by autonomous measurement).

As the method by the remote measurement, there are a method of using an optical image sensor (e.g., JP2000-182058A, JP2002-8043 A, or JP 10-74249 A), a method of using a magnetic sensor, and the like.

As the method by the remote measurement can execute measurement only in a space in which the sensor installed outside is functional, its measuring range is limited. Depending on a sensor type, there is a space in which the sensor cannot be installed. For example, a method of tracking by the optical image sensor with an LED or the like as a mark cannot be used outdoors when it is bright. A method of tracking a marker attached to a measuring target by applying an infrared light (e.g., VICON by Vicon Motion Systems Inc.) cannot be used outside, either. In the case of using a magnetic sensor (e.g., Motion Star ASCENSION Inc.), measurement is impossible in a magnetically fluctuating environment.

On the other hand, the method by the autonomous measurement has an advantage of no restrictions on a measuring range. Measuring methods are so-called mechanical types to measure elongation/contraction of a wire, a change in an angle of a bar, relative distances among sensors attached to four limbs, or the like (e.g., by Gypsy Spice Inc.), and they are similar in that joint angles are measured.

All the methods need to attach the sensor to each limb, restricting a joint motion itself in many cases. As the sensor itself is large, its appearance gives an uncomfortable feeling, and thus the sensor is not suitable for outdoor use. Accuracy of angle measurement is low, and thus unsatisfactory for highly accurate operation measurement.

Incidentally, a recent progress made in semiconductor microfabrication technology has made available an acceleration sensor and an angular velocity sensor called MEMS inertia sensors at reasonable prices. A compact inertia measuring instrument constituted of such a MEMS inertia sensor is inferior in accuracy to a conventional inertia navigation instrument or gyro used for posture control of an aircraft or the like. However, it has a compact and light-weight feature.

Thus, it is not impossible now to attach the sensor to the body thereby measuring a human posture. However, to calculate a moving distance or a direction from an output of the inertia sensor, integration must be carried out twice in the case of the acceleration sensor, and once in the case of the angular velocity sensor. Accordingly, small errors accumulate with time caused by a fluctuation in a still output which accompanies electric noise in the sensor output, a shift in gravity axis, or a change in a surrounding environment such as a temperature. A drift phenomenon occurs in a measuring position even in a still state. As a method of correcting this drift, use of an external signal of an ultrasonic wave, magnetism, a light, or the like is general. For example, in motion tracking (refer to U.S. Pat. Nos. 6,176,837 and 6,474,159), an instrument for determining a direction or a position of a body, or a head mount display instrument for reproducing a human posture in a virtual space of a computer is realized by a system for correcting an error of an inertia measuring instrument by an ultrasonic wave. However, those methods impose spatial restrictions after all as in the case of the aforementioned method by the remote measurement. An attempt has been made to measure a joint angle of a human body only by an inertia sensor (refer to JP 11-325881 A). However, there are restrictions in that the sensor must be attached as close as possible to both ends of the joint, and usable places are limited to a hand, a leg, and the like.

Measurement of a motion of a human body is necessary in many fields. In management engineering, there is an example of measuring and analyzing a working motion of a worker in detail to improve working efficiency. In computer graphics, to represent a real human motion, the human motion must be accurately measured. In a medical field, measurement of a motion must be accurately carried out to quantitatively understand how a motion of a patient is improved in a process of rehabilitation or the like. Thus, the human body motion measuring system is expected to be used for various purposes, and some measuring systems have been developed. However, in measurement, most of the systems inevitably impose restrictions on human behaviors which become measuring targets. Besides, the number of systems in which measuring costs are high is not small.

With the foregoing in mind, the present invention proposes a system which can correct the aforementioned drift phenomenon of the measuring position and execute efficient measurement with restrictions as small as possible on contents or places of motion (e.g., not only indoor but also outdoor free spaces) regarding a human to be measured.

DISCLOSURE OF THE INVENTION

In an acceleration sensor or an angular velocity sensor, an output voltage is generally referred to as a zero point voltage when input acceleration or an input angular velocity is zero. As described above, however, this zero point voltage fluctuates because of an influence of external disturbances such as an environmental temperature of the sensor. Thus, errors accumulate, resulting in data of a value indicating a state completely different from original real data after a passage of predetermined time. To correct such a drift phenomenon, the present invention focuses on possibility of determining a direction of gravity by the acceleration sensor in any state.

That is, a direction of gravity G1 is determined in an initial still state by the acceleration sensor. The direction indicated by G1 is always unchanged if the aforementioned drift phenomenon occurs. In reality, however, when a moving object to which the acceleration sensor is attached moves in a coordinate axis, the direction is gradually changed with time by the drift phenomenon.

Accordingly, after a passage of optional time, the acceleration sensor is set in a still state to determine a direction of gravity, a true direction of gravity judged from determined data at this time is compared with the direction of gravity G1 affected by the drift phenomenon, a difference therebetween is regarded as an error, and the error is subtracted from a determined value to correct an error of a measured value.

In this case, correction targets are not only the direction of gravity but also all directions in the coordinates. For example, if a 3-axis angular velocity sensor is further provided, a value measured by the angular velocity sensor is also corrected according to the error. In other words, in X, Y and Z directions, when a direction of gravity is Y, correction of the Y direction is accompanied by correction of the X and Z directions. This similarly applies to two-dimensional coordinates.

A method of the present invention can be used for a position determining instrument or a posture determining instrument equipped with at least an acceleration sensor capable of determining a gravity method, and further applied to a motion capture system (motion measuring instrument). According to the present invention, based on an output from the acceleration sensor or an angular velocity sensor, for example, a vector direction is determined, and a posture of a measuring target and thus a position on the coordinates are measured, whereby the motion can be measured at the end.

According to such an instrument, to measure a position or a posture in a specific coordinate system according to output values from the acceleration sensor and the angular velocity sensor, and to determine a motion of the moving object to which the sensors are attached, on a computer, after-motion gravitational direction measuring means for determining a direction of gravity in an initial still state by the acceleration sensor, and moving the initial direction of gravity associatively with a motion in the coordinate system of the instrument to measure a direction of gravity after the motion, still time gravitational direction measuring means for measuring a direction of gravity in a still state of the acceleration sensor after a passage of optional time, difference determining means for comparing the still state direction of gravity measured by the still time gravitational direction measuring means with the after-motion direction of gravity measured by the after-motion gravitational direction measuring means by the motion thus far to determine a difference therebetween, correcting means for correcting measuring data to specify a motion or a position of the moving object according to the difference obtained by the difference determining means, and the like are realized as function realizing means by a program.

The motion capture system includes a determining unit equipped with an acceleration sensor and an angular velocity sensor. This determining unit is attached to a main point of a measuring target. If a measuring target has an arm rotated around a joint as in the case of a human body or a robot arm, the determining unit is attached to a middle point of the arm.

The system includes a computer for processing data. In this computer, a specific coordinate system is preset. The coordinate system may be two-dimensional or three-dimensional. However, to measure an object motion in a real world such as a motion of a human body, the three-dimensional coordinate system is preferable.

A basic posture of the measuring target is defined beforehand on the coordinate system, and a sensor attaching position is specified further on the definition. If displacement of position data obtained according to a motion of the measuring target is added with the position set as an original point, how the measuring target has moved from the basic posture is known. In other words, motion measurement is enabled. If there is no error in a value from the sensor, the motion can be accurately measured. However, an output fluctuation caused by a temperature change or the like is accompanied by a drift phenomenon as described above. For example, it is supposed that an output 0 v is defined beforehand as an output indicating an x axis direction. However, an output which should be originally 0 becomes +2 v because of a subsequent temperature change. 0 v is defined to be the x axis direction while the value of +2 v should originally indicate the x axis. Thus, the x axis direction judged from the measuring data is shifted by −2 v from the original x axis direction. Accumulation of such drift phenomena causes great deviation of a motion to be measured from the original posture with a passage of time.

Accordingly, the method of the present invention is applied to correct the deviation.

Assuming that a direction of gravity is always constant on Earth, a direction of gravity determined by the acceleration sensor of the still state means that a measured value always indicates accurate direction of gravity. In other words, supposing that Y1 is an acceleration sensor output of a direction of gravity measured at a certain point of time, Y1' is a direction of gravity after a passage of predetermined time which is accumulated with the Y1 as a start point, and Y2 is an output of the acceleration sensor of the still state after the passage of predetermined time, Y1' and Y2 are considered to basically indicate the same direction of gravity at that time.

Then, if Y2−Y1'=k (k≠0) is established, generation of an error in the sensor output value by a drift phenomenon can be understood. Thus, even if the error k occurs in all the directions, by considering the error k, the error k is subtracted in all the 3-axis directions to restore the original posture.

According to the present invention, a system may be employed to capture an output from the sensor into the computer by wire. Preferably, however, a transmitter is disposed in the sensor unit, and a receiver is disposed on the computer side, whereby the sensor output is wirelessly taken into the computer. This is preferable because it imposes no restrictions on the motion of the measuring target.

The present invention is preferably applicable by a moving object motion measuring method for a 3-axis direction motion measuring instrument equipped with a 3-axis acceleration sensor and a 3-axis angular velocity sensor.

Here, the method includes: specifying a relative positional relation between a frame constituting the object or a frame equivalent portion and a sensor coordinate system to attach the sensors to the moving object; taking an initial posture in which a positional relation with a world coordinate system is known, initializing the instrument, and determining an initial direction of gravity with respect to the sensor coordinate system by the acceleration sensor based on initial posture information; using a relative positional relation among a direction of the rotated sensor coordinate system, the angular velocity sensor, and the frame to determine a direction of the frame, setting an original point as a start point, determining a position of a joint which is an adjacent frame connection portion based on a direction and a length of each frame, determining a position of an adjacent joint based on the determined joint position and the direction and length of the frame to measure how the frame has moved, and simultaneously rotating, since the initial direction of gravity is relatively rotated when the angular velocity sensor is rotated associatively with a motion of the moving object, the initial direction of gravity in the sensor coordinate system associatively with rotation of the sensor to calculate a direction of gravity G1; and measuring a direction of gravity G2 by the 3-axis acceleration sensor when the moving object is set in a still state, comparing the after-motion direction of gravity G1 after a passage of predetermined time with the still-time direction of gravity G2, determining an error based on a difference therebetween, determining an error changing parameter based on the error information according to time-change characteristics of a drift error of the angular velocity sensor, and correcting motion measuring data of the moving object thereafter according to the error changing parameter.

In each of the above method and instrument, the accuracy is more increased when a magnetic direction sensor is provided, an initial magnetic direction is determined by the magnetic direction sensor, the initial magnetic direction is changed associatively with the motion of the moving object, a magnetic direction is then measured by the magnetic direction sensor after a passage of optional time, an error is measured based on a difference between the after-motion magnetic direction and the magnetic direction after the passage of the optional time, and the error is corrected associatively with error measurement in a direction of gravity by the acceleration sensor.

In this case, if the moving object is a human body, and the frame is a skeleton, a motion of the human body can be measured.

If the motion of the human body is a measuring target, according to the present invention, a compact 6-freedom inertia measuring instrument constituted of a compact 3-axis acceleration sensor and a 3-axis yaw rate sensor is attached to the body such as a head, four limbs (left and right upper arms, left and right front arms, left and right hand backs, left and right thighs, left and right lower thighs, or left and right leg backs), or a body (back or waist), whereby a relative angle of each potion of the human body such as the head, the four limbs or the body is measured to accurately measure/reproduce the motion of the human body. This system is within autonomous measurement. It can be used under any environment as long as the sensor is attached, imposing no limitation on measuring space. In other words, it is possible to measure a free human motion in all spaces outdoors and indoors.

Measurement is possible not by attaching the sensor for each joint but only by attaching the sensors one by one to the head, the four limbs and the body by fixing tools such as supporters. Accordingly, the number of attached sensors can be reduced as compared with the method based on joint angle measurement, and a free joint motion is not restricted. The sensor itself can be miniaturized, and thus its attachment is easy.

Thus, the present invention is applicable to the following purposes.

1) Motion Analysis of Worker at Factory or Construction Site

By analyzing a motion of a worker to build a good motion work procedure or working environment of no loads or wastes, it is possible to improve production efficiency and to build a safety and health standard motion.

2) Abnormality Determination Accompanying Dangerous Work

Work at a nuclear power plant or a blast furnace of a steel plant, cleaning in a gas tank, work in a refrigerator of a food center, cave checking inspection in a coal mine, a tunnel or a subway, or the like is accompanied by a danger leading to a loss of a human life. Accordingly, abnormalities must be identified as early as possible to find countermeasures. However, in many cases, such a working place is a sealed space, a special environment which cannot be approached unless special equipments are carried, or an area in which an infrastructure of a camera or a sensor for determining abnormalities cannot be built. By an attached type human body motion measuring system, the motion of the human body is measured to enable understanding of a situation and determination of abnormalities.

3) Acquisition of Three-dimensional Information for Computer Graphics

Various motions of the human motion can be measured three-dimensionally under many environments, and a more real motion can be reproduced by CG because of small restrictions on the joint motion. Moreover, the present invention can be applied to a human body motion input type game.

4) Acquisition of Three-dimensional Data for Medical Treatment and Sports

A state of caring/rehabilitation/work (posture) is measured and represented by a numerical value. This is a system for measuring a motion of a patient to check a treatment effect or quantitatively understand a progressing situation, thereby supporting technique improvement or the like. This is also a system for analyzing a three-dimensional motion of an athlete or a dancer, thereby supporting improvement of techniques etc.

When the motion determining instrument equipped with the acceleration sensor and the angular velocity sensor is attached to the human body, acquisition of the sensor attaching angle to the limb of the human body and the relative positional relation between the external coordinate system which becomes a reference for human body motion measurement and the sensor based on a relative relation between the direction of gravity obtained from the acceleration sensor and a specific human body posture which becomes a reference facilitates the attaching of the motion determining instrument to the human body.

According to the present invention, with the foregoing configuration, it is possible to properly correct the error caused by the drift phenomenon. As a result, more accurate motion measurement can be carried out.

BRIEF DESCRIPTION OF THE DRAWINGS

FIG. 4 is a diagram showing an arrangement of a 6-freedom sensor box and a substrate;

FIG. 12 is a photo showing an animated operation of a lower limb;

BEST MODE FOR CARRYING OUT THE INVENTION

Hereinafter, an embodiment of the present invention will be described with reference to the accompanying drawings.

First, a sensor unit used by the embodiment is a compact 6-freedom inertia measuring instrument (referred to as 6-freedom sensor box hereinafter) which has outputs of 3-axis acceleration and a 3-axis angular velocity.

Figure 1:
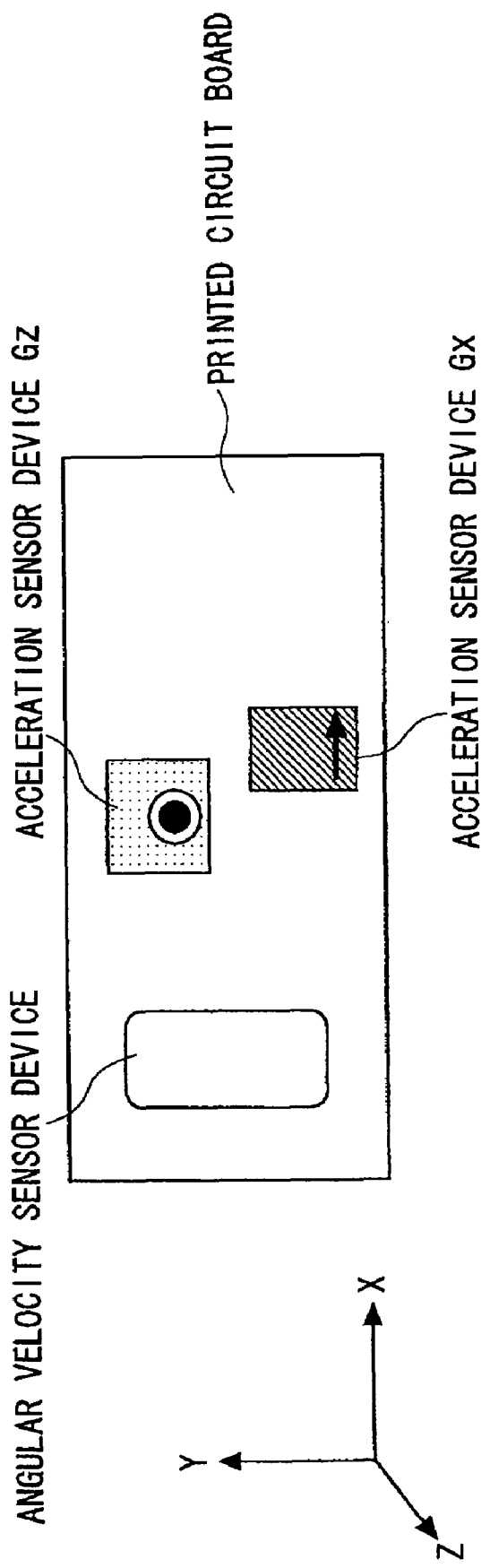
FIG. 1 is a diagram showing a combine sensor which includes an acceleration sensor and an angular velocity sensor.

This 6-freedom sensor box is configured by using three combine sensors which combine acceleration and angular velocity sensors. As shown in FIG. 1, the combine sensor includes an acceleration sensor for determining acceleration Gx parallel to a printed circuit board, an acceleration sensor device for determining acceleration Gz vertical to the printed circuit board, and one angular velocity sensor device for determining an angular velocity around a y axis arranged on the printed circuit board.

Figure 2:
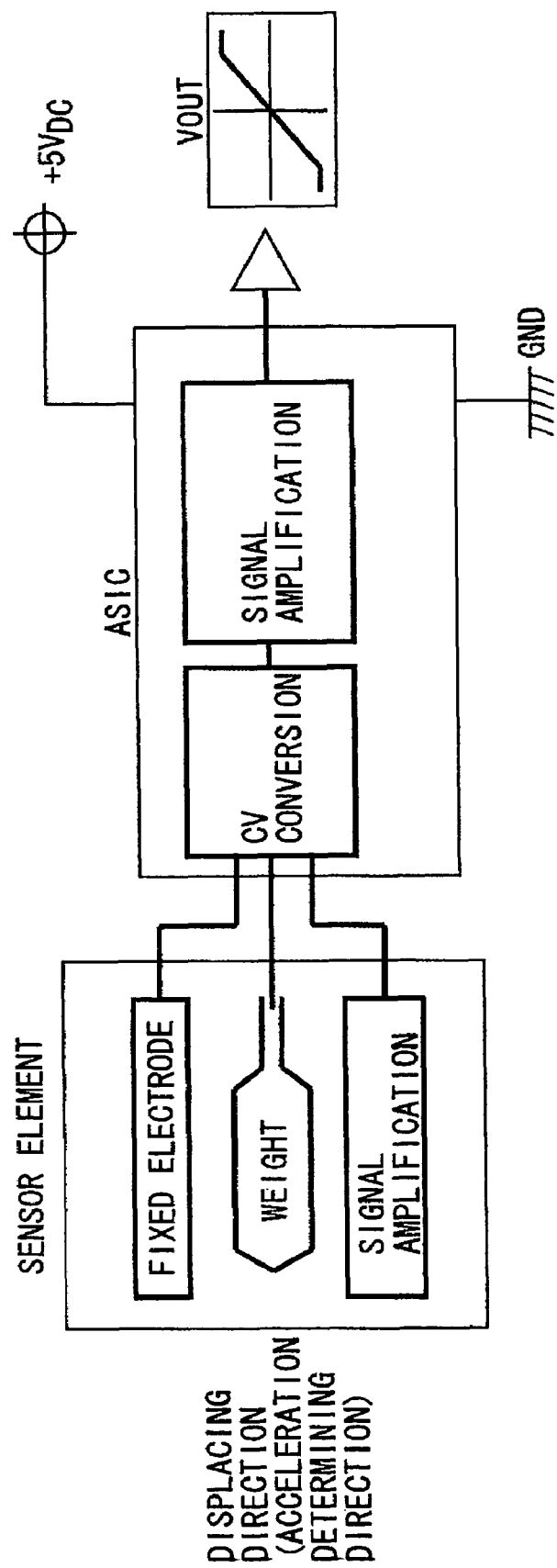
FIG. 2 is a circuit diagram of the acceleration sensor.

FIG. 2 shows the acceleration sensor. This acceleration sensor device is a semiconductor capacity type by VTI Inc., a capacity type low-acceleration sensor packaged by premolding, and a capacitance type for making a very small weight to be displaced by acceleration on a silicon substrate by a semiconductor microfabrication technology, and reading a change in a gap between a movable weight (movable electrode) and a fixed electrode as a change in capacitance. In addition to the capacitance type of the embodiment by the VTI Inc., capacitance type devices by Silicon Sensing Systems Inc., and Analog Device Inc., a piezoelectric resistance type device by Hitachi Metal Inc., and the like are available, but the invention is not limited to these.

A detailed configuration of the angular velocity sensor is not shown, but an angular velocity sensor of a double tuning fork or vibrator type quartz system by BEI Inc., is used here. As the angular velocity sensor, there is a vibration gyro which uses a phenomenon of vertical Coriolis force generated in a vibration direction by application of acceleration to a vibrated object, and a vibrator of piezoelectric ceramics, or the like. In addition to the vibration turning fork type of the embodiment by the BEI Inc., a tuning bar vibrator type (Mitsubishi Electric Corporation, Murata Manufacturing Company, Ltd.), a vibrator ring type (Silicon Sensing Inc.), and the like are available.

Figure 3:
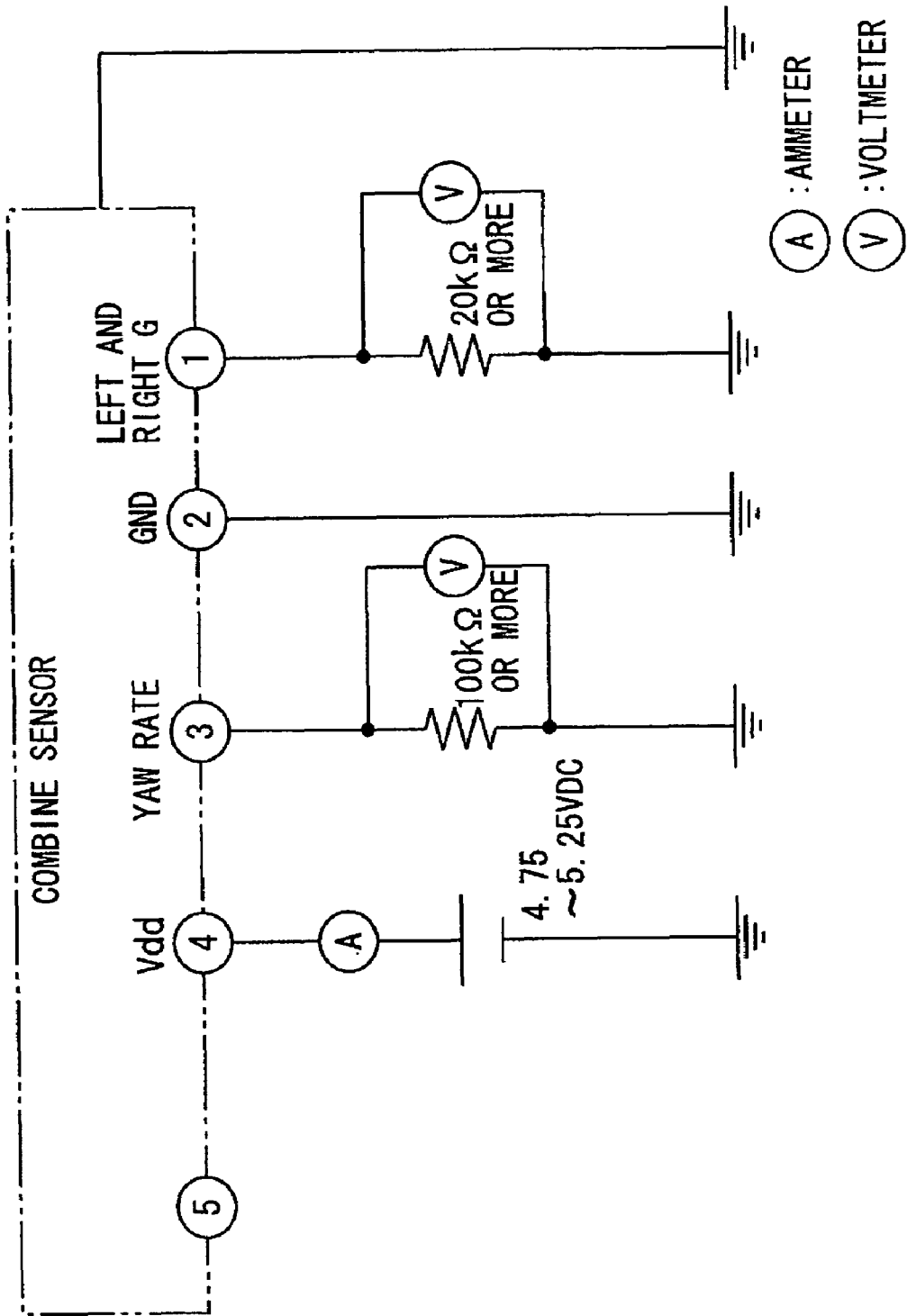
FIG. 3 is a circuit diagram showing an output from the combine sensor.

FIG. 3 shows a circuit of the combine sensor driven by applying a DC voltage of 5 V (4.75 to 5.25 V) to a terminal (4). A terminal (2) is grounded, resistance of 100 kΩ or more is connected to a terminal (3), and resistance of 20 kΩ or more is connected to a terminal (1). Then, from the terminal (3), an angular velocity is output as a voltage value between resistance terminals of 100 kΩ or more. From the terminal (1), acceleration is output as a voltage value between resistance terminals of 20 kΩ or more.

FIG. 4 shows a configuration of a 6-freedom sensor box used for an experiment. This sensor box was configured by arranging the three combine sensor substrates mentioned above sterically as shown so as to obtain outputs of a 3-axis angular velocity and 3-axis acceleration orthogonal to each other. A 1-axis angular velocity (yaw) and x-axis acceleration were taken out from a substrate (1), a 1-axis angular velocity (roll), y axis acceleration, and z axis acceleration were taken out from a substrate (2), and a 1-axis angular velocity (pitch) were taken out from a substrate (3), all as voltage outputs. An output from each sensor was fetched in a notebook PC by an AD conversion card, DAQCard-6024E, manufactured by National Instruments Inc.

Figure 5:
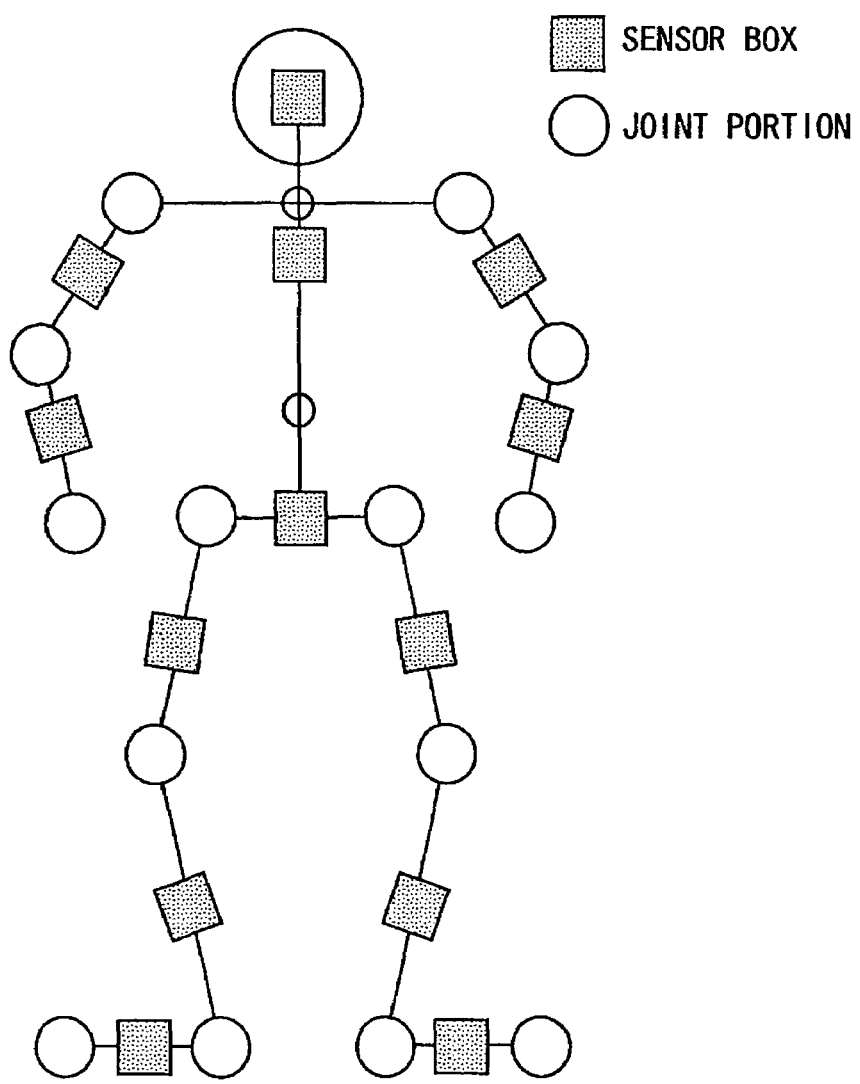
FIG. 5 is a diagram showing a human body portion to which the sensor box is attached.

A plurality of 6-freedom sensor boxes configured in the aforementioned manner are prepared, and attached to limbs. In FIG. 5, ■ indicates a sensor box attaching position, which is basically set between joints of the limbs so that a Y axis can be in a direction of each bone.

A local coordinate system is set for the 6-freedom sensor box. Next, each direction angle is determined for an external reference coordinate system (world coordinates).

Figure 6:
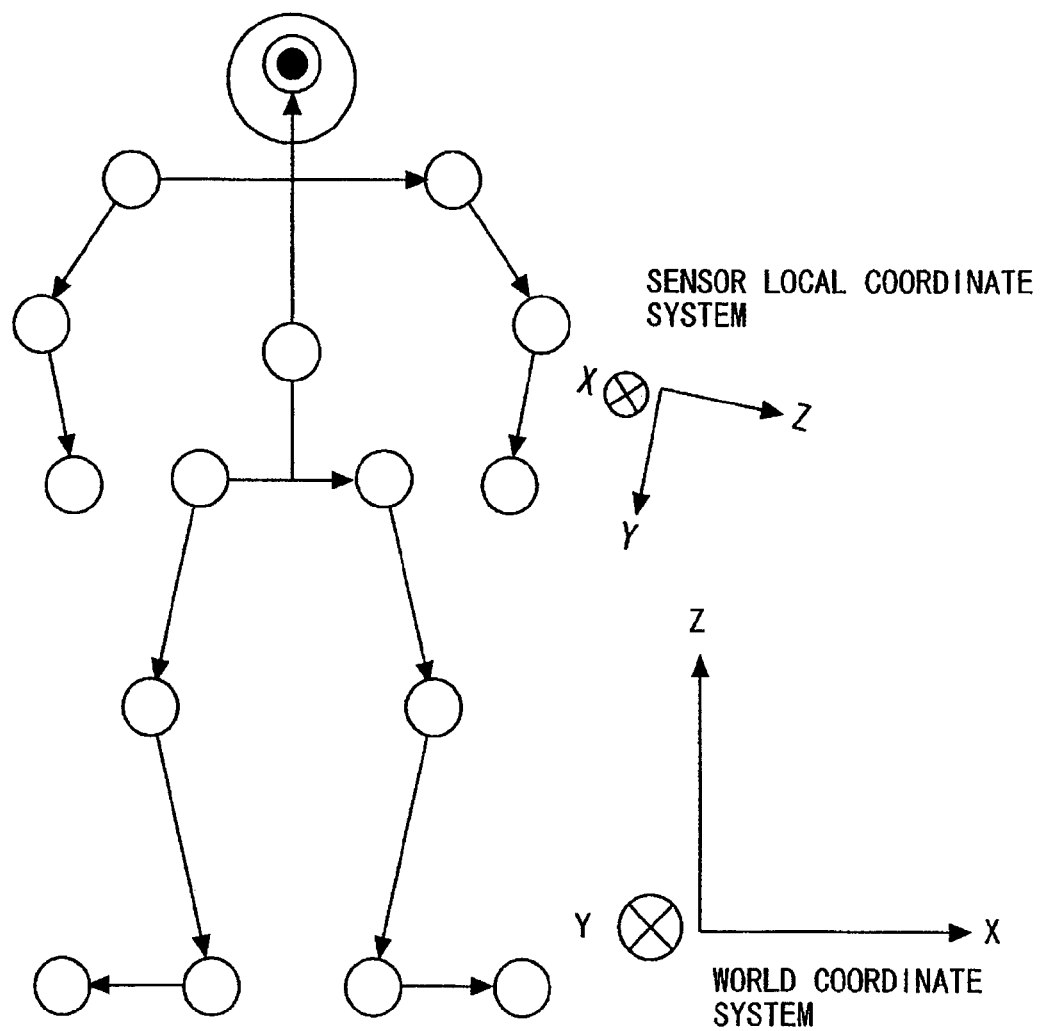
FIG. 6 is a diagram showing a sensor coordinate system and a world coordinate system in a correlated manner.

In this case, a structure of a human body is represented by a skeleton model (FIG. 6). The skeleton model is created beforehand by making bone and joint class objects on a computer and registering them as human body class objects.

Then, the Y axis direction of the 6-freedom sensor box is set along the bone. Accordingly, a direction angle of each bone constituting the skeleton is provided from the 6-freedom sensor box.

Figure 7:
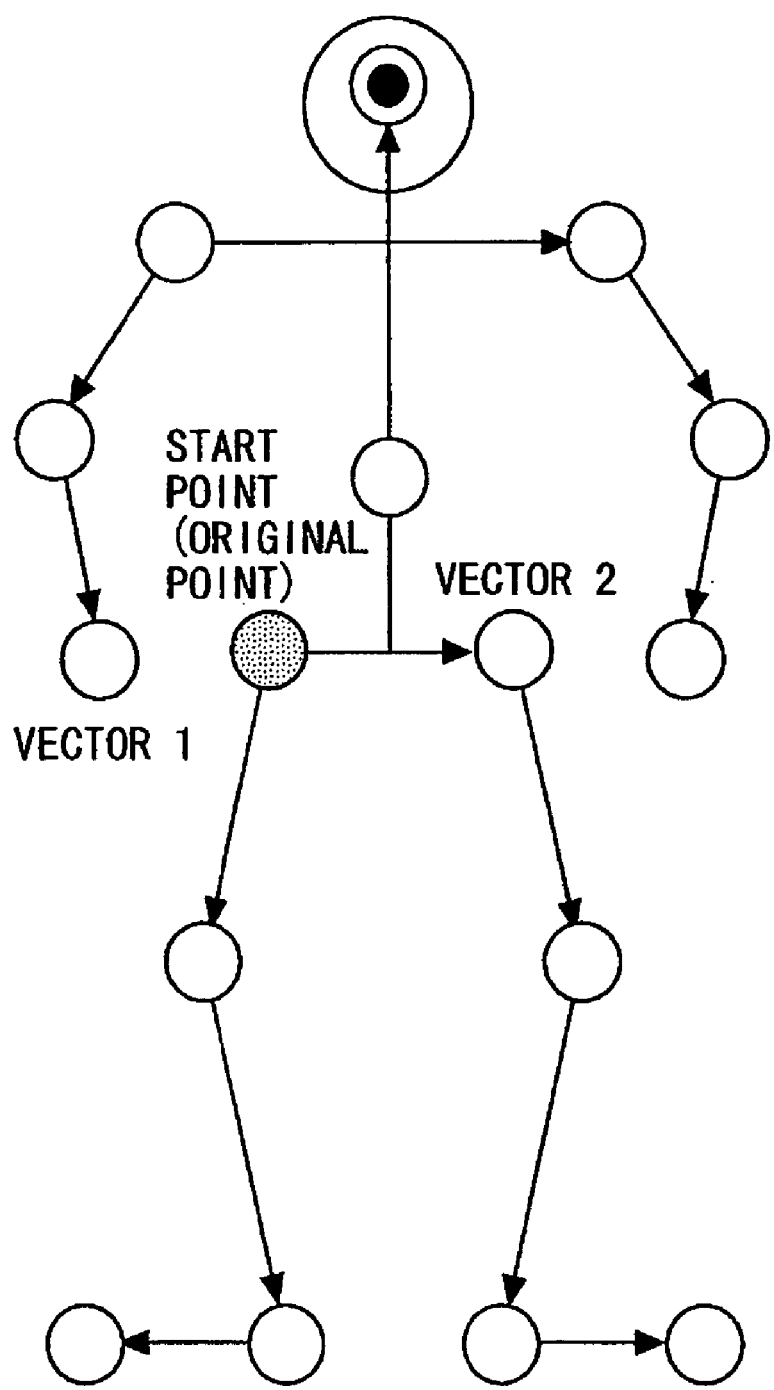
FIG. 7 is a diagram of a method of calculating coordinates of each node (joint)

A bone direction vector is determined by measuring a bone length beforehand. It is to be noted that the bone length is substituted for by a length between joints. As shown in FIG. 7, further, a calculation start point is decided on an optional node (joint) or bone, whereby bone direction vectors are sequentially added together to determine coordinates from the start node to each node. In FIG. 7, vectors are determined with one hip joint set as a start point.

In this case, the following problems occur.

Accurate measurement needs accurate determination of an initial attaching angle between the sensor and the four limbs, and accurate determination of a positional relation between the sensor and the external reference coordinate system. However, it is not easy to directly measure a relative angle between a measuring axis of the sensor and a direction of the four limbs or the like.

In angle measurement by a yaw rate sensor, measuring errors accumulate to deteriorate accuracy over time. This is called a drift error. The drift error must somehow be corrected in the middle of measurement.

Accordingly, the present invention provides the following solutions.

For accurate measurement of a sensor attaching angle or the like, use of a 3-axis acceleration sensor enables determination of a direction of gravity, and thus this is used. As a direction of a gravity on a coordinate system which becomes reference coincides with one axis, restricting conditions on the sensor attaching angle can be obtained from the direction of gravity.

Additionally, a direction (direction angle) perpendicular to the direction of gravity must be provided. This direction angle can be determined by taking a posture such as standing upright or sitting on a chair to identify a relative direction angle between the external reference coordinate system and the four limbs or the body after the sensor is attached. Simultaneously, relative attaching angle between the four limbs or the body and the sensor can be determined.

Moreover, accurate estimation can be made by combing magnetic direction sensors through the same procedure.

As in the aforementioned case, several kinds of proper still postures are taken in the middle of operation, and a direction of gravity is determined by the 3-axis acceleration sensor each time, thereby correcting a drift error.

Alternatively, the 3-axis acceleration sensor/yaw rate sensor is further combined with the magnetic direction sensor to execute the same procedure, thereby enabling accurate estimation.

Next, referring to FIGS. 8 and 9, motion measurement of the human body and its correcting method of the present invention will be described.

Figure 8:
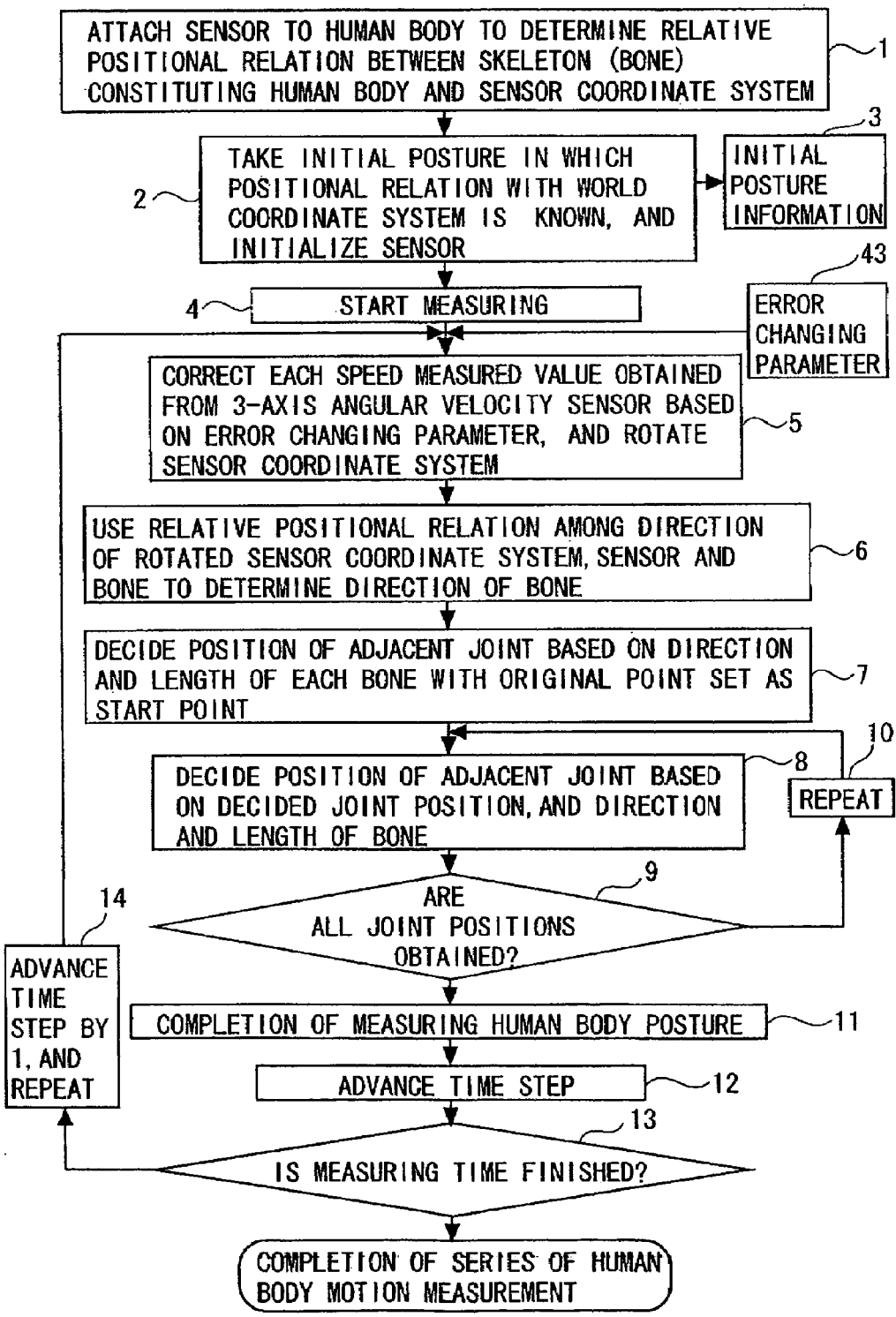
FIG. 8 is a flowchart showing a human body motion measuring procedure.

Referring to FIG. 8, first, in a step 1, the sensor is attached to the human body to determine a relative positional relation between a skeleton (bones) constituting the human body and a sensor coordinate system. Subsequently, in a step 2, an initial posture in which a positional relation with a world coordinate system is known is taken to initialize the sensor. This initial posture information is stored in a memory (step 3). It is to be noted that a human body model is preset on the computer as described above as a premise.

After completion of the initialization, measurement is started in a step 4.

In this case, first, each velocity measured value obtained from the 3-axis angular velocity sensor is corrected based on an error changing parameter, and then the sensor coordinate system is rotated (step 5). In initial measurement, no correction is made because the error changing parameter is 0.

Next, a bone direction is determined by using a direction of the rotated sensor coordinate system and the relative positional relation between the sensor and the bone (step 6). Further, in a step 7, with an original point set as a start point, a position of an adjacent joint is determined based on a direction and a length of each bone. Then, in a step 8, a position of an adjacent joint is determined based on the determined joint position and the direction and the length of the bone. This operation is repeatedly executed until all joint positions are determined (steps 9 and 10). Accordingly, how arms or legs have moved is measured (step 11). Then, a time step is advanced (step 12). When the time step reaches a preset measuring time, the measuring time comes to end (step 13), thereby completing a series of operation measurement. On the other hand, when the measuring time does not come to an end in the step 13, the process returns to the step 5 to repeat the steps 5 to 12.

Figure 9:
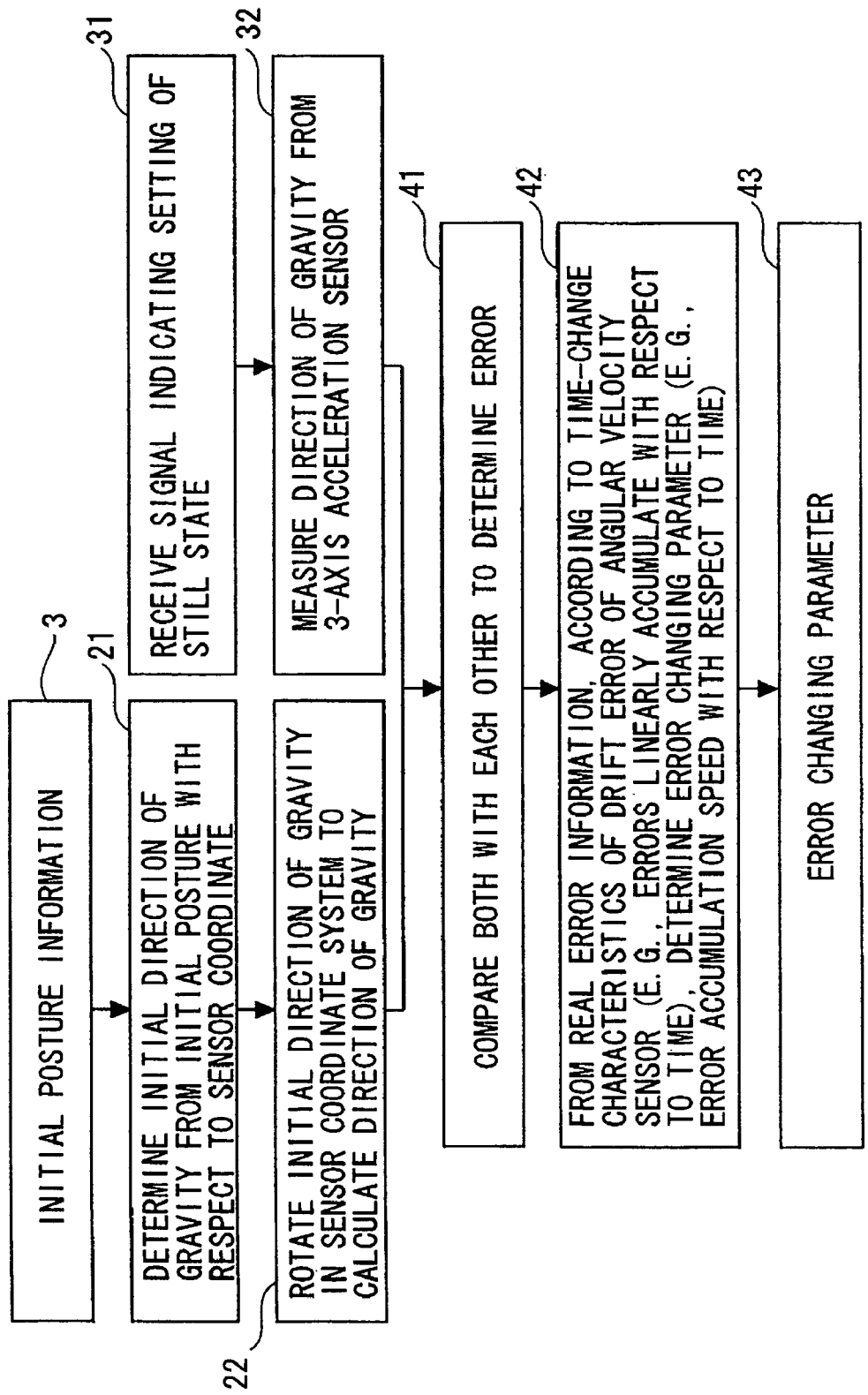
FIG. 9 is a flowchart showing a method of correcting measuring data.

In a flowchart of FIG. 9, in the measurement of FIG. 8, an error changing parameter is determined to correct errors accumulated over time due to a drift phenomenon.

In this case, during execution of a routine of FIG. 8, the initial posture information stored in the memory is fetched, and an initial direction of gravity is determined with respect to the sensor coordinate system from the initial posture (step 21). When a motion of the human body is accompanied by rotation of the sensor, the initial direction of gravity is relatively rotated. Thus, by rotating the initial direction of gravity in the sensor coordinate system associatively with the rotation of the sensor, a direction of gravity is calculated (step 22). The direction of gravity with a passage of predetermined time obtained as a result takes a value which contains errors caused by the drift phenomenon.

In the meantime, when the human body stops during the measurement, a program receives a signal indicting setting of a still state (step 31). The signal indicating the still state is generated, for example, as follows. After the still state has been set, an output signal from the sensor has no fluctuation: even if there is a fluctuation, it is limited to an extremely small width. Accordingly, when its output time continues for a predetermined time, a still state is judged to issue a still state signal.

In the case of the still state, a direction of gravity is measured from the 3-axis acceleration sensor (step 32). The direction of gravity measured here is specified by a true value as there has been no processing.

Thus, the direction of gravity after the passage of predetermined time specified in the step 22 is compared with the true direction of gravity specified in the step 32, and an error is determined from a difference therebetween (step 41).

Then, from this actual error information, an error changing parameter (e.g., error accumulation speed with respect to time) is determined according to time-change characteristics (e.g., errors linearly accumulate with respect to time) of the drift error of the angular velocity sensor (step 42).

The error changing parameter is stored in the memory (step 43), and used for the correction executed in the step 5 of FIG. 8.

Accruing to the routine of FIGS. 8 and 9, the error changing parameter is determined for each still state, and the measuring error is corrected based on the error changing parameter for each measurement. Thus, the error is always corrected to measure the motion, whereby the human body motion can be measured more accurately.

EXAMPLE

Next, a specific example of measuring a motion of a lower body and reproducing a sitting motion of a human on a chair in a computer will be described.

1.) Experiment Instrument

As described above, such a sensor box was manufactured and used that three combine sensor substrates including two acceleration axes and one yaw rate axis were used, and an acceleration sensor and yaw rate sensor were arranged to be three-dimensionally orthogonal to each other, thereby enabling acquisition of outputs of three acceleration axes and three yaw rate axes. An output from each sensor was fetched in a notebook PC by an AD conversion card, DAQCard-6024E, manufactured by National Instrument Inc.

2) Attachment of Sensor Box

Figure 10:
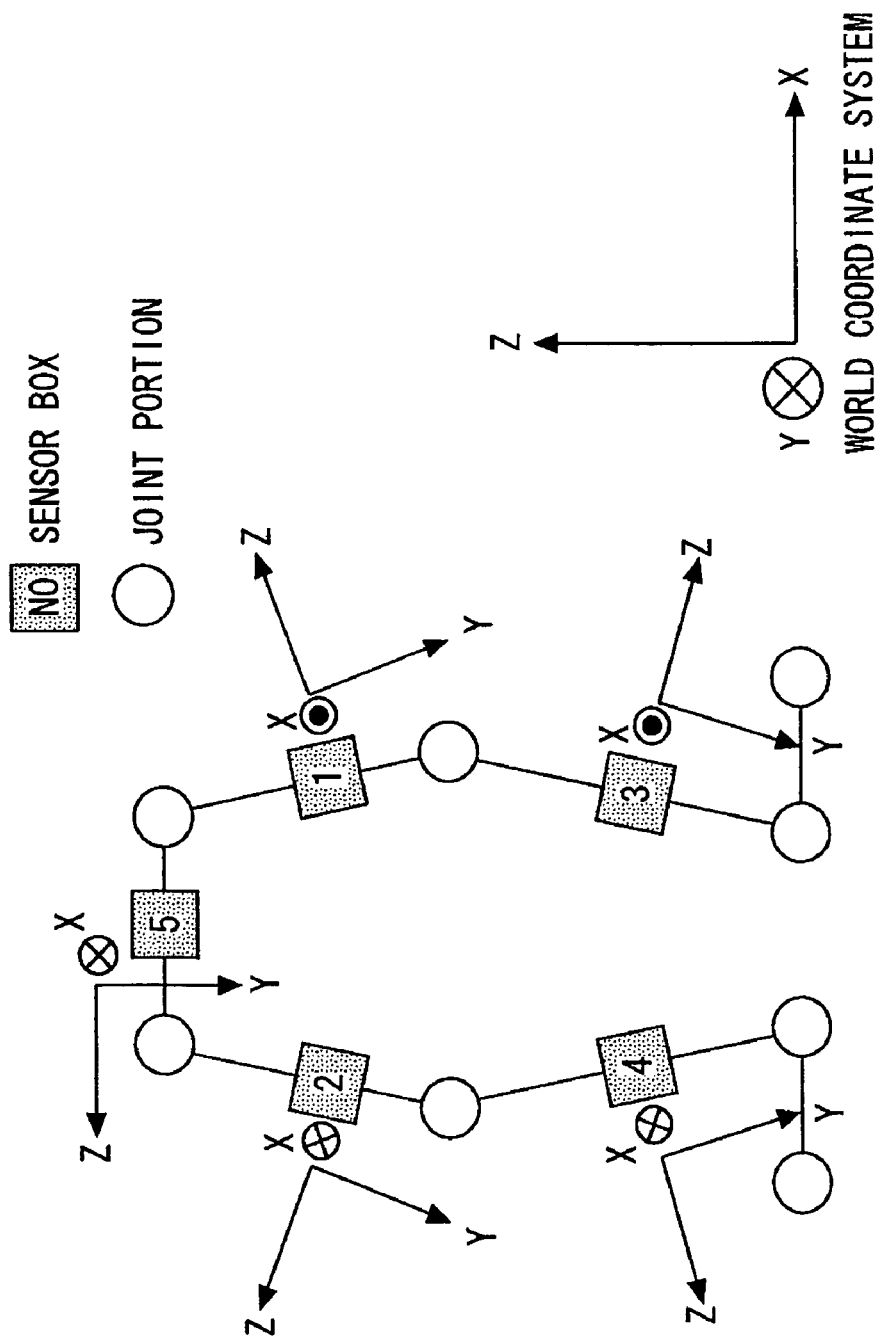
FIG. 10 is a diagram showing a sensor box attaching place and local and world coordinates.

Five compact sensor boxes were attached to respective portions (waist, left and right thighs, and left and right lower thighs) shown in FIG. 10 by using supporters or magic tapes (registered trademark).

In FIG. 10, ○ indicates a joint (joint portion), and ■ indicates a sensor box. As it was not attached to a real bone, the sensor box was attached to an outer surface of a human body such as the outside of the left and right thighs or the outside of the left and right lower thighs.

3) Measurement

To correct an attaching angle of the sensor box and drift errors accumulated over time by determining a direction of gravity from an output of a 3-axis acceleration sensor, a pose of periodically stopping still in upright posture was taken.

First, (1) an initial still state was taken in upright posture. Next, (2) a motion of bending knees from the upright position to sit on a chair was repeated continuously by three times. (3) A still state was set again for about 15 sec. Subsequently, the motions of (2) and (3) were repeated to finish the process.

4) Calculation Processing and Animation

Figure 11:
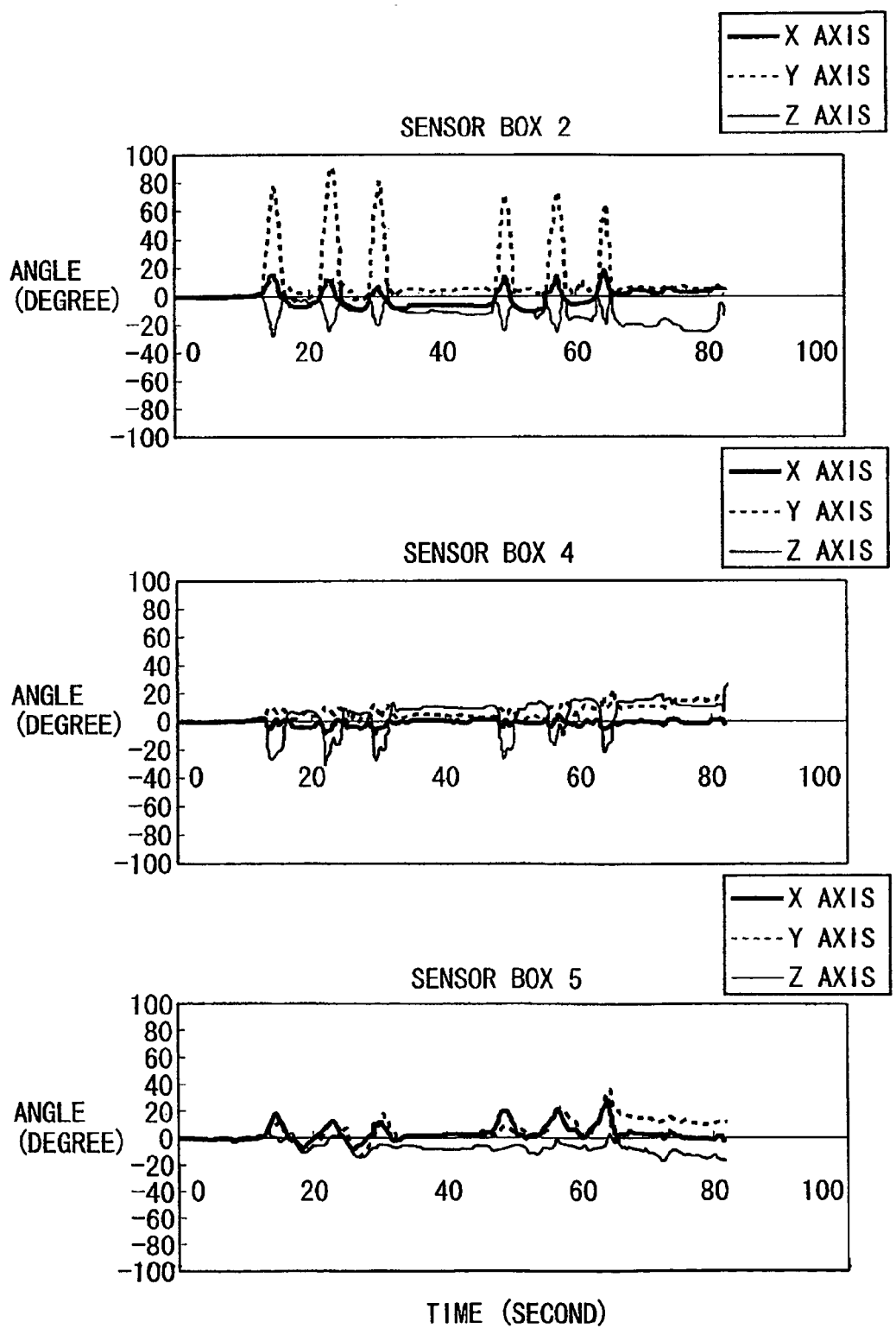
FIG. 11 is a diagram showing angle conversion data.

Data obtained by integrating an output of the yaw rate sensor of each sensor box and converting it into an angle is shown (FIG. 11).

FIG. 12 shows a situation of processing a measuring operation based on each angle data according to the flowchart and animating the operation. In FIG. 12, an upper stage shows an upright state, a middle stage shows a kneeling state, and a lower stage shows a sitting state.

The aforementioned example will be described more in detail.

First, a relation between a direction of gravity detected from the axis acceleration sensor and an angle integrated from the yaw rate sensor will be described.

Figure 13:
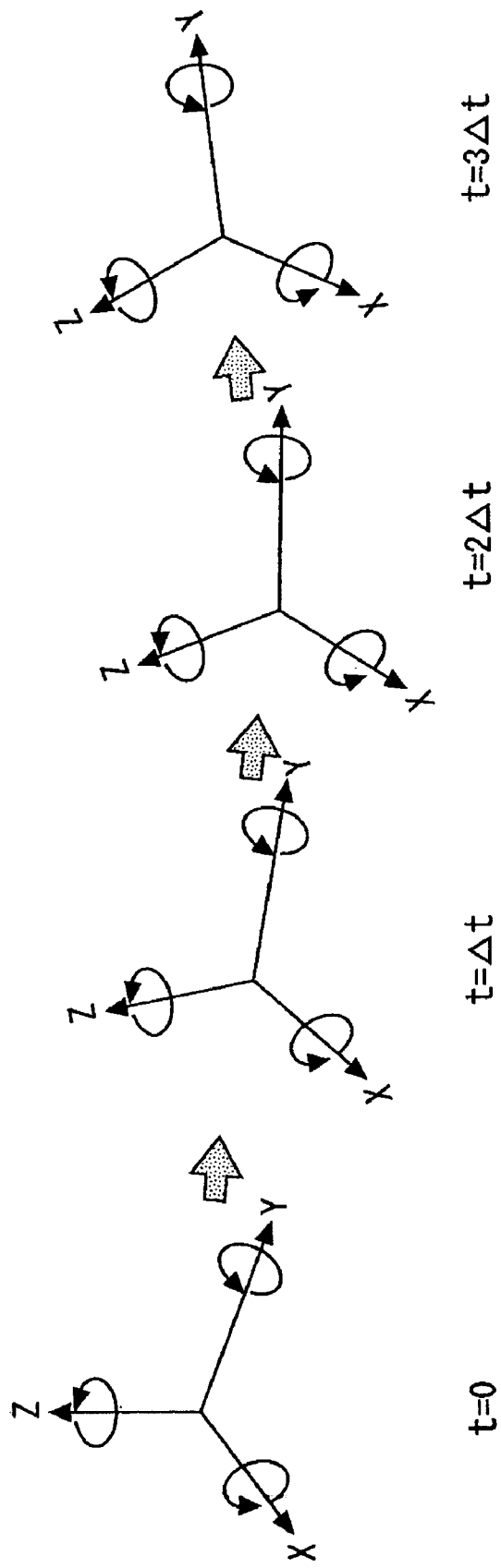
FIG. 13 is a diagram showing a rotational change of a sensor axis.

FIG. 13 shows a state of a rotational change of a sensor axis, and it is presumed that an axis of a 3-axis accelerometer and an axis of the yaw rate sensor have correctly been calibrates.

<t=0 (Initial State)>

When world coordinate system (X, Y, Z) is rotated by ($\alpha_0$, $\beta_0$, $\gamma_0$), $e_{x0}$, $e_{y0}$, $e_{zo}$ are set (sensor coordinate system). In other words, $\vec{X}$: vector on world coordinate system $\vec{Xs}$: vector represented by sensor coordinate system $$\vec{X} = R(\alpha_0, \beta_0, \gamma_0) \cdot \vec{Xs} \quad \text{(equation A) and,}$$

$$\vec{Xs} = R^{-1}(\alpha_0, \beta_0, \gamma_0) \cdot \vec{X} \quad \text{(equation B)}$$

R (($\alpha_0$, $\beta_0$, $\gamma_0$)) is a rotation matrix. In this case, a roll angle ($\alpha$), a pitch angle ($\beta$), and a yaw angle ($\gamma$) are rotated in this order. R ( . . . ) is defined as follows.

$$R_\alpha = \begin{pmatrix} 1 & 0 & 0 \\ 0 & \cos\alpha & -\sin\alpha \\ 0 & \sin\alpha & \cos\alpha \end{pmatrix}, R_x = \begin{pmatrix} \cos\beta & 0 & \sin\beta \\ 0 & 1 & 0 \\ -\sin\beta & 0 & \cos\beta \end{pmatrix}, \quad \text{(equation 1)}$$

$$R_\gamma = \begin{pmatrix} \cos\gamma & -\sin\gamma & 0 \\ \sin\gamma & \cos\gamma & 0 \\ 0 & 0 & 1 \end{pmatrix}$$

A direction on the world coordinate system becomes (0, 0, −1) This is represented as follows on the sensor coordinate system from the equation B:

$$\vec{Xs} = R^{-1}(\alpha_0, \beta_0, \lambda_0) \cdot \begin{pmatrix} 0 \\ 0 \\ -1 \end{pmatrix} \quad \text{(equation 2)}$$

At this time, an output vector of the 3-axis acceleration sensor is normalized to 1. If an acceleration sensor output vector is represented by the following equation 3, $$\vec{As} = \begin{pmatrix} As_x \\ As_y \\ As_z \end{pmatrix}_{t=0}, |As| = 1 \quad \text{(equation 3)}$$

$\vec{Xs} = \vec{As}$ should be set.

For example, if a rotational angle of the sensor coordinate system has a roll angle alone while pitch and yaw angles are both zero, the following equation 4 is established, $$\vec{Xs} = \begin{pmatrix} 1 & 0 & 0 \\ 0 & \cos\alpha & -\sin\alpha \\ 0 & \sin\alpha & \cos\alpha \end{pmatrix} \begin{pmatrix} 0 \\ 0 \\ -1 \end{pmatrix} = \begin{pmatrix} 0 \\ -\cos\alpha \\ -\sin\alpha \end{pmatrix} = \begin{pmatrix} As_x \\ As_y \\ As_z \end{pmatrix} \quad \text{(equation 4)}$$

$\alpha$ can be determined from a gravity vector. However, if the yaw angle alone is rotated, the following equation 5 is established, $$\vec{Xs} = \begin{pmatrix} \cos\gamma & -\sin\gamma & 0 \\ \sin\gamma & \cos\gamma & 0 \\ 0 & 0 & 1 \end{pmatrix} \begin{pmatrix} 0 \\ 0 \\ -1 \end{pmatrix} = \begin{pmatrix} 0 \\ 0 \\ -1 \end{pmatrix} = \begin{pmatrix} As_x \\ As_y \\ As_z \end{pmatrix} \quad \text{(equation 5)}$$

and $\gamma$ (yaw angle) is not decided. This is because a yaw rate component is not included in a column of z axis component of the rotation matrix of $R^{-1}$ ($\alpha_0$, $\beta_0$, $\gamma_0$). In other words, it is a function of a roll angle and a pitch angle alone represented by the following equation 6.

$$\vec{Xs} = \begin{pmatrix} Xs(\alpha, \beta) \\ Ys(\alpha, \beta) \\ Zs(\alpha, \beta) \end{pmatrix} \quad \text{(equation 6)}$$

That is, there is no yaw rate information, and a yaw angle of an initial value cannot be decided. Thus, it must be decided separately. This method will be described in a section of initial value setting.

<Passage of Time Only by t=Δt>

If a yaw rate is ($\bar{\alpha}, \bar{\beta}, \bar{\gamma}$) with t=Δ, a rotational angle from t=0 to t=Δt is represented by the following equation 7:

$$\left( \frac{1}{2}\bar{\alpha} \cdot \Delta t, \frac{1}{2}\bar{\beta} \cdot \Delta t, \frac{1}{2}\bar{\gamma} \cdot \Delta t \right) \quad \text{(equation 7)}$$

At this time, the yaw rate is zero with t=0; This is also represented by the following equation 8:

$$(\Delta\alpha_1, \Delta\beta_1, \Delta\gamma_1) \quad \text{(equation 8)}$$

The yaw rate takes a form in which world coordinates rotate around a sensor coordinate axis. In other words, it is represented by the following equation 9:

$$\vec{Xs}_{t=0} \rightarrow \vec{Xs}_{t=\Delta t} \quad \text{(equation 9)}$$

$$\vec{Xs}_{t=\Delta t} = R^{-1}(\Delta\alpha, \Delta\beta, \Delta\gamma) \cdot \vec{Xs}_{t=0}$$

$$= R^{-1}(\Delta\alpha, \Delta\beta, \Delta\gamma) \cdot R^{-1}(\alpha_0, \beta_0, \gamma_0) \cdot \vec{X}$$

A gravitational direction vector at this time is represented by the following equation 10:

$$\vec{Xs}\Big|_{t=\Delta t} = R^{-1}(\Delta\alpha_i, \Delta\beta_i, \Delta\gamma_i) \cdot R^{-1}(\alpha_0, \beta_0, \gamma_0) \cdot \begin{pmatrix} 0 \\ 0 \\ -1 \end{pmatrix} \quad \text{(equation 10)}$$

Calibration is possible as $$\vec{Xs_g}\Big|_{t=\Delta t}$$

contains information of $\Delta\gamma$. In other words, the following is established:

$$\vec{Xs_g}\Big|_{t=\Delta t} = \begin{pmatrix} Xs(\alpha_0, \beta_0, \Delta\alpha, \Delta\beta, \Delta\gamma) \\ Ys(\alpha_0, \beta_0, \Delta\alpha, \Delta\beta, \Delta\gamma) \\ Zs(\alpha_0, \beta_0, \Delta\alpha, \Delta\beta, \Delta\gamma) \end{pmatrix} = \begin{pmatrix} As_x \\ As_y \\ As_z \end{pmatrix}_{t=\Delta t}$$

$\vec{As}$ is an output value (unit vector) from the 3-axis acceleration sensor with $t=\Delta t$.

From the foregoing, it is apparent that $\alpha_0$, $\beta_0$, $\Delta\alpha$, $\Delta\beta$, and $\Delta\gamma$ can be calibrated based on the output from the accelerometer. However, $\gamma_0$ must be given separately. This method will be described in the section of initial value setting.

<Error Correcting Method>

Figure 14:
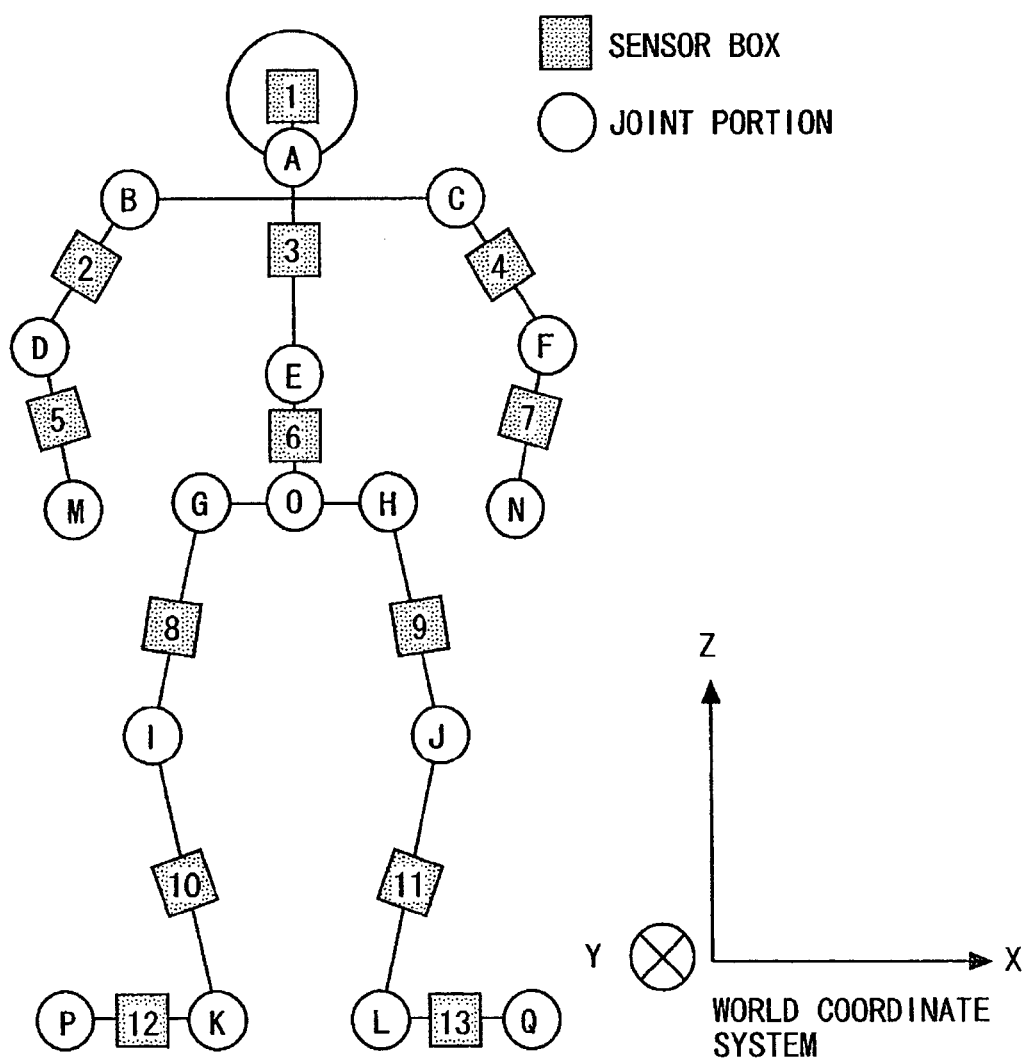
FIG. 14 is a diagram showing a skeleton model and world coordinates.

Next, initial setting and an error correcting method for measurement will be described. FIG. 14 shows a skeleton model and world coordinates. Initial state setting is executed based on a relation between the skeleton model and the world coordinates. The following three are presumed for setting an initial state.

Each sensor is correctly attached to each "bone" of the skeleton model.

For example, one axis vector of a sensor local coordinate system correctly coincides with a bone direction. However, directions of two axis vectors other than the coincident vector are not known.

A length of each bone is measured beforehand.

It is possible to cause a person to be tested to take a certain posture which becomes an "initial state". At this time, the following conditions have conceivably been established:
1. GH//KL (waist bone and bones of both toes are parallel)
2. GH//BC (waist bone and bones of both toes are parallel)
3. BDM (arm), CFN (waste), GIK (leg), HJL (leg), and AEQ (backbone) are straight
4. BC (shoulder)//GH (waist)//KL (toe)//floor

*For simplicity, both legs, both arms, and the backbone may be vertical to the floor.

The initial state established from the aforementioned presumption must satisfy the following two requirements.

First requirement: directions of all the bones in the skeleton model (direction of a coordinate system of sensors attached to the bones with respect to world coordinates: FIG. 14) can be decided.

Second requirement: three-dimensional coordinates of each node can be calculated when angles of all the bones are established.

For the first requirement, initial yaw angles of all the bones must be decided.

(Method 1) At the time of the aforementioned initial posture, yaw angles of all the bones are separately measured. Alternatively, an initial posture is taken so that yaw rates can be decided.

(Method 2) A method of deciding in combination with the second requirement. However, it can be used only partially.

Figure 15:
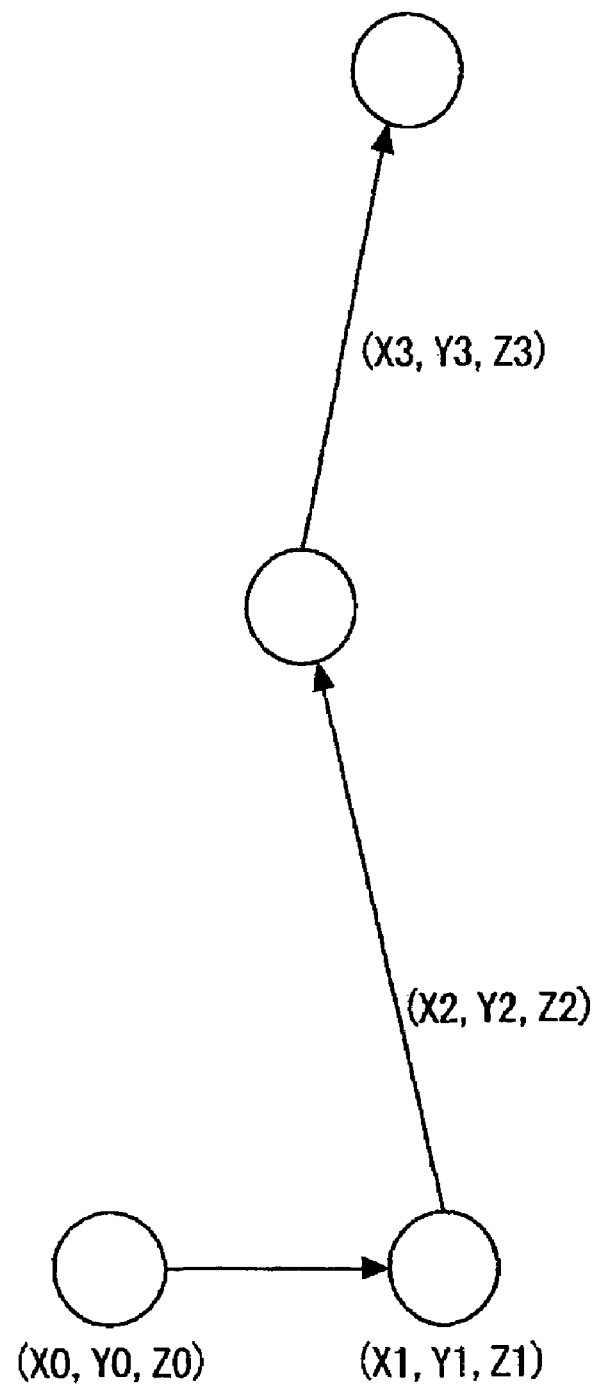
FIG. 15 is a diagram showing a bone-direction vector.

For the second requirement, if bone inclination alone is known as shown in FIG. 15, it means that direction vectors ($\Delta x$, $\Delta y$, $\Delta z$) alone are known.

However, as the user needs each node and a three-dimensional coordinate value, an initial value (coordinate initial value/length of each bone, or the like) is always necessary. It is an initial posture that provides this initial value. However, initial values can be provided at different places.

Figure 16:
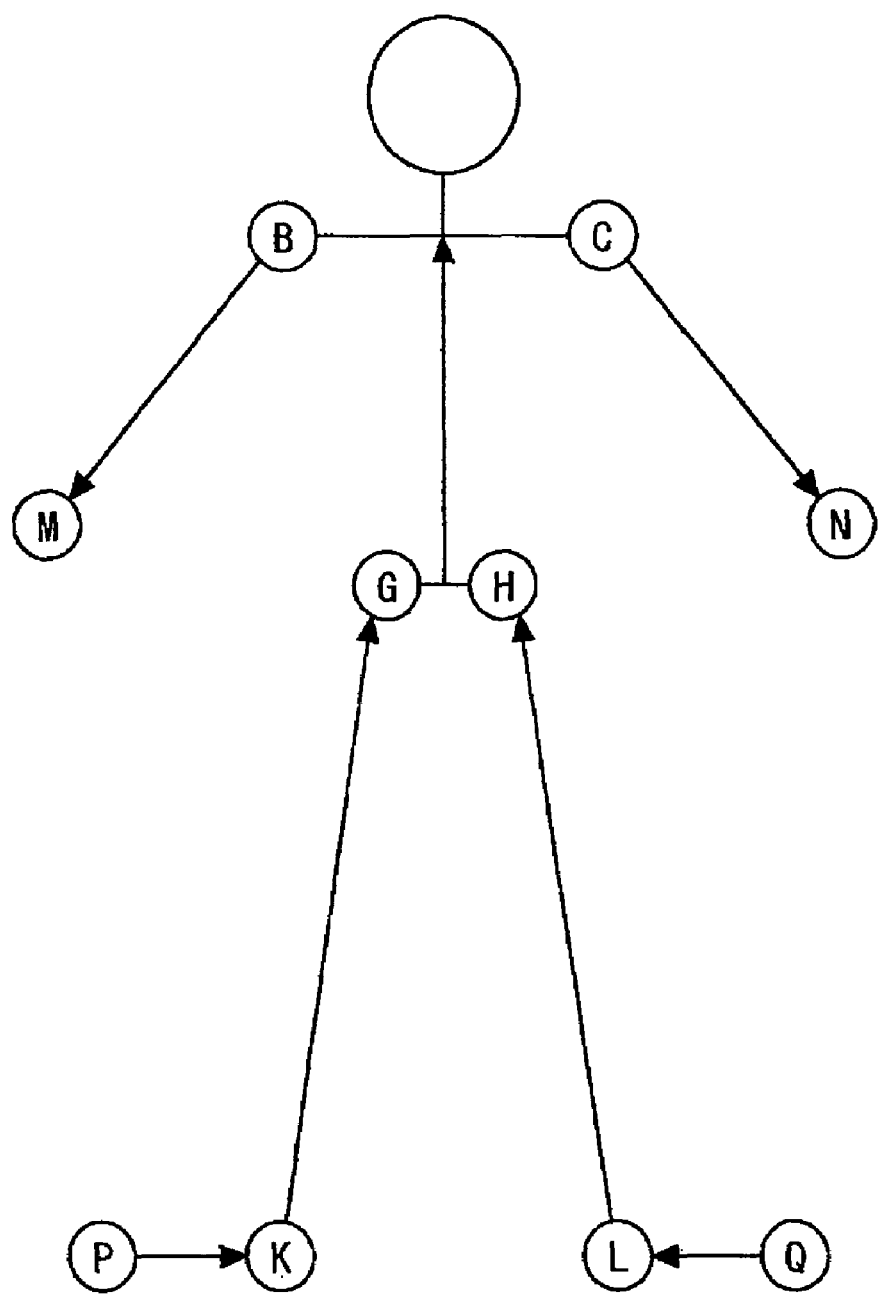
FIG. 16 is a simplified diagram of an integration procedure.

For example, as shown in an integration procedure simplified diagram of FIG. 16, a place which both legs (P, Q) touch is decided beforehand (integration original point). At a waist (G, H) above the P, Q, geometric conditions must be satisfied (e.g., GH//KL, GH=40 cm, or the like). Sequential integration to vector directions of the "bones" enables determination of a position of each node. In this case too, GH//BC becomes a necessary condition.

Figure 17:
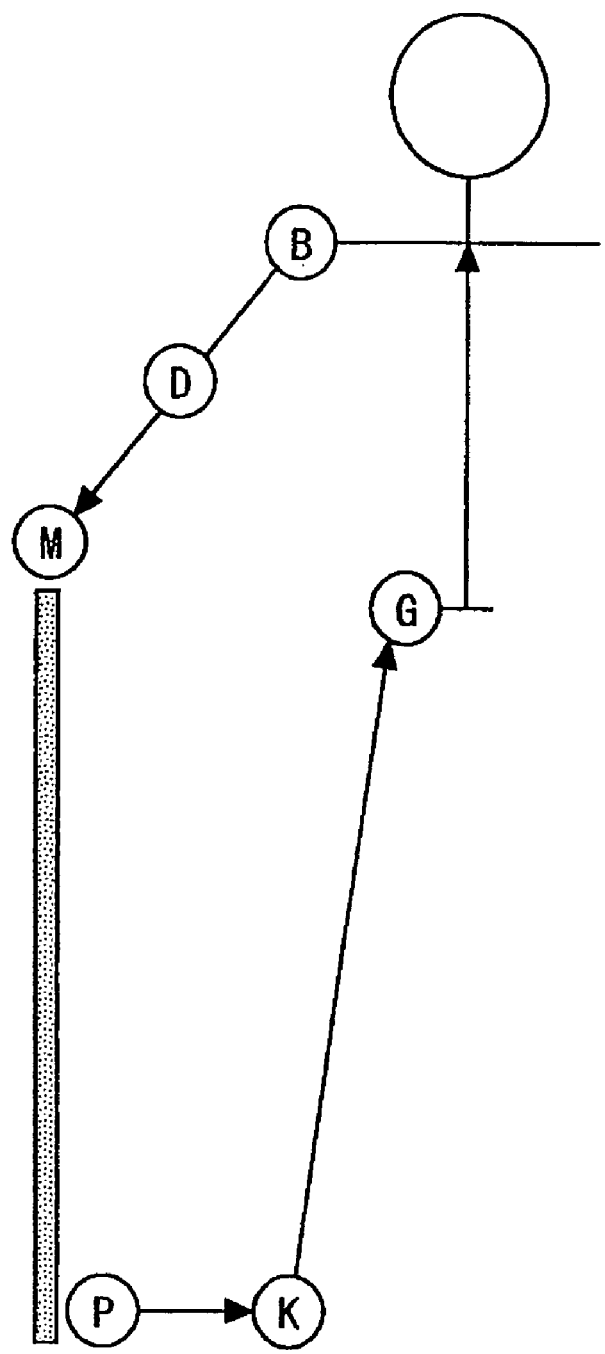
FIG. 17 is a diagram of additional conditions.

As a further added condition, a hand is placed on a bar (or cord) as shown in FIG. 17, whereby a hand coordinate value can be decided relatively to the leg. This value can be used as a condition to decide an initial yaw angle of an arm portion.

<Correcting Method During Motion>

For correction during motion, a correcting method 1 is mainly applied. However, a correcting method 2 can also be used as an auxiliary method.

<Correction Method 1>

A "still state" is inserted during the motion, and reference is made to the direction of gravity to enable correction. A rotational amount (initial rotational amount) with $t=0$ is set to $(\alpha_0, \beta_0, \gamma_0)$ A period of rotation by $(\Delta\alpha_1, \Delta\beta_1, \Delta\gamma_1)$ from $t=0$ is set to $t=\Delta t$, and time of further rotation by $(\Delta\alpha_2, \Delta\beta_2, \Delta\gamma_2)$ is set to $t=2\Delta t$. This is repeated thereafter.

With $t=2\Delta t$, the following equation is used to determine a point (vector) $\vec{X}$ on a sensor coordinate system (represented by sensor coordinate system) for a point (vector) represented by $\vec{Xs}$ on a world coordinate system.

*$R^{-1}(\alpha, \beta, \gamma)$ is a vector rotational matrix on (x, y, z) axes.

$$\vec{Xs}\Big|_{t=2\Delta t} = R^{-1}(\Delta\alpha_2, \Delta\beta_2, \Delta\gamma_2) \cdot \quad \text{(equation 11)}$$
$$R^{-1}(\Delta\alpha_1, \Delta\beta_1, \Delta\gamma_1) \cdot R^{-1}(\alpha_0, \beta_0, \gamma_0) \cdot \vec{X}$$

With $t=N\cdot\Delta t$, multiplication by the rotational matrix is repeated.

In this case, gravity data from the acceleration sensor becomes as follows.

$$\vec{Xs}\Big|_{t=2\Delta t} = R^{-1}(\Delta\alpha_2, \Delta\beta_2, \Delta\gamma_2) \cdot R^{-1}(\Delta\alpha_1, \Delta\beta_1, \Delta\gamma_1) \cdot \quad \text{(equation 12)}$$

-continued $$R^{-1}(\alpha_0, \beta_0, \gamma_0) \cdot \begin{pmatrix} 0 \\ 0 \\ -1 \end{pmatrix} = \begin{pmatrix} As_x \\ As_y \\ As_z \end{pmatrix}_{t=2\Delta t}$$

An underlined portion (*) of the equation 12 is an output unit vector of the 3-axis acceleration sensor in an initial state. $\vec{As}$ is set as a normalized output vector (direction of gravity) of the accelerometer.

When generalized, this equation is represented by the following equation:

$$\vec{Xs}_{t=i\Delta t} = \left( \prod_{i=1}^{N} R^{-1}(\Delta\alpha_i, \Delta\beta_i, \Delta\gamma_i) \right) \cdot R^{-1}(\alpha_0, \beta_0, \gamma_0) \cdot \begin{pmatrix} 0 \\ 0 \\ -1 \end{pmatrix} = \begin{pmatrix} As_x \\ As_y \\ As_z \end{pmatrix}$$

As $\gamma_0$ is not included in the equation 13 (refer to appendix), $\gamma_0$ cannot be calibrated based on the direction gravity.

For a drift term, it is presumed that drifts accumulate in proportion to time. In other words, it may be represented by a (t)=$a_0$+at.

When converted into a yaw rate, it is presented by the following equation:

$$\Delta\alpha_i = \Delta\tilde{\alpha}_i + \Delta C_\alpha + \epsilon_\alpha \quad \text{(equation 14)}$$

$\Delta\tilde{\alpha}_i$: true yaw rate
$\Delta C_\alpha$: constant magnitude error (unidirectional)
$\epsilon_\alpha$: random error component having an average of zero
Similarly, $$\Delta\beta_i = \Delta\tilde{\beta}_i + \Delta C_\beta + \epsilon_\beta$$

$$\Delta\gamma_i = \Delta\tilde{\gamma}_i + \Delta C_\gamma + \epsilon_\gamma$$

Further approximation is represented by the following equation:

$$\Delta\alpha_i \approx \Delta\tilde{\alpha}_i + \Delta C_\alpha$$

$$\Delta\beta_i \approx \Delta\tilde{\beta}_i + \Delta C_\beta$$

$$\Delta\gamma_i \approx \Delta\tilde{\gamma}_i + \Delta C_\gamma \quad \text{(equation 15)}$$

From the equation 15, a change in gravitational direction vector in a rotational angle including the drift term can uniformly be generalized as follows:

$$\vec{Xs}_{t=i\Delta t} = \left( \prod_{k}^{i} R^{-1}(\Delta\tilde{\alpha}_k + \Delta C_\alpha, \Delta\tilde{\beta}_k + \Delta C_\beta, \Delta\tilde{\gamma}_k + \Delta C_\gamma) \right) \cdot$$

$$R^{-1}(\alpha_0, \beta_0, \gamma_0) \cdot \begin{pmatrix} 0 \\ 0 \\ -1 \end{pmatrix}$$

(equation 16)

A difference is obtained between a result $\vec{Xs}$ of the gravity vector change of the equation 16 and an output vector $\vec{As}$ (true value) of the accelerometer at the same time.

$$\text{difference vector} = \vec{As} - \vec{Xs} = \begin{pmatrix} \Delta x \\ \Delta y \\ \Delta z \end{pmatrix} \quad (17)$$

$\Delta C_\alpha$, $\Delta C_\beta$, $\Delta C_\gamma$, $\alpha_o$, and $\beta_o$ must be decided to minimize a sum of squares of a difference vector presented by the equation 17 until i=1 to N (as long as it is in a still state).

$$\sum_{i=1}^{N} (\Delta x^2 + \Delta y^2 + \Delta z^2)_{t=i\Delta t}$$

However, $\gamma_0$ cannot be decided by this method. It must be decided by initial value setting.

<Connecting Method 2>

In a "still" state, (true) yaw rates around the axis, i.e., outputs of the yaw rate sensor, all become zero. In other words, a yaw rate output value in the "still state" (for about several seconds) must be equal to the aforementioned $\Delta C_\alpha$, $\Delta C_\beta$, or $\Delta C_\gamma$. This information is additionally used to improve correction accuracy, or to check a correction result.

INDUSTRIAL APPLICABILITY

The present invention is a system for measuring the motion of a human or another moving object, and can be used in broad fields such as motion analysis of workers at a factory or a construction site, abnormality determination in dangerous work, and CG reproduction of a human motion.

The invention claimed is:

1. A difference correcting method for a posture determining instrument equipped with at least an acceleration sensor to determine a posture and/or a position in a predetermined coordinate system, the method comprising:
   determining a direction of gravity in an initial still state by the acceleration sensor;
   moving the initial direction of gravity associatively with a motion of the posture determining instrument in the coordinate system to calculate a direction of gravity after the motion;
   setting the acceleration sensor in a still state to measure a direction of gravity after a passage of optional time;
   comparing the measured direction of gravity of the still state with the direction of gravity after the motion in the coordinate system, and regarding a difference therebetween as an error;
   correcting a measured value of the posture and/or the position in the coordinate system based on the error; and
   outputting the corrected measured value.

2. A motion determining instrument of a moving object, equipped with an acceleration sensor and an angular velocity sensor to measure a posture and/or a position in a specific coordinate system according to output values from the sensors, and to determine a motion of the moving object to which the sensors are attached, the motion determining instrument comprising:
   after-motion gravitational direction measuring means for determining a direction of gravity in an initial still state by the acceleration sensor, and moving the initial direction of gravity associatively with a motion of a determining instrument in the coordinate system to measure a direction of gravity after the motion;

still time gravitational direction measuring means for measuring a direction of gravity in a still state of the acceleration sensor after a passage of optional time;

difference determining means for comparing the direction of gravity of the still state measured by the still time gravitational direction measuring means with the direction of gravity after the motion measured by the after-motion gravitational direction measuring means to determine a difference therebetween; and correcting means for correcting measured data for specifying a motion or a position of the moving object according to the difference obtained by the difference determining means.

3. A motion determining instrument according to claim 2, characterized in that the acceleration sensor is a 3-axis acceleration sensor, and the angular velocity sensor is a 3-axis angular velocity sensor.

4. A method of attaching a motion determining instrument to a human body, the motion determining instrument being equipped with an acceleration sensor and an angular velocity sensor to measure a posture and/or a position in a specific coordinate system according to outputs from the sensors, and to determine a motion of the moving object to which the sensors are attached, the method comprising:

determining an attaching angle of the sensor to a limb of the human body;

determining a relative positional relation between an external coordinate system which becomes a reference for human body motion measurement and the sensor based on a relative position between a direction of gravity obtained from the acceleration sensor and a specific posture of the human body which becomes a reference; and outputting the determined relative positional relation.

5. A moving object motion measuring method for a 3-axis direction motion measuring instrument equipped with a 3-axis acceleration sensor and a 3-axis angular velocity sensor, the method comprising:

specifying a relative positional relation between a frame constituting the object or a frame equivalent portion and a sensor coordinate system to associate the sensors to the moving object;

taking an initial posture in which a positional relation with a world coordinate system is known, initializing the instrument, and determining an initial direction of gravity with respect to the sensor coordinate system by the acceleration sensor based on initial posture information;

using a relative positional relation among a direction of the rotated sensor coordinate system, the angular velocity sensor, and the frame to determine a direction of the frame, setting an original point as a start point, determining a position of a joint which is an adjacent frame connection portion based on a direction and a length of each frame, determining a position of an adjacent joint based on the determined joint position and the direction and length of the frame to measure how the frame has moved, and simultaneously rotating, since the initial direction of gravity is relatively rotated when the angular velocity sensor is rotated associatively with a motion of the moving object, the initial direction of gravity in the sensor coordinate system associatively with rotation of the sensor to calculate a direction of gravity G1;

measuring a direction of gravity G2 by the 3-axis acceleration sensor when the moving object is set in a still state, comparing the after-motion direction of gravity G1 after a passage of predetermined time with the still-time direction of gravity G2, determining an error based on a difference therebetween, determining an error changing parameter based on the error information according to time-change characteristics of a drift error of the angular velocity sensor, and correcting motion measuring data of the moving object thereafter according to the error changing parameter; and outputting the corrected motion measuring data of the moving object.

6. A method according to claim 1 or 5, characterized in that a magnetic direction sensor is provided, an initial magnetic direction is determined by the magnetic direction sensor, the initial magnetic direction is changed associatively with the motion of the moving object, a magnetic direction is then measured by the magnetic direction sensor after a passage of optional time, an error is measured based on a difference between the after-motion magnetic direction and the magnetic direction after the passage of the optional time, and the error is corrected associatively with error measurement in a direction of gravity by the acceleration sensor.

* * * * *

UNITED STATES PATENT AND TRADEMARK OFFICE
CERTIFICATE OF CORRECTION

PATENT NO. : 7,233,872 B2
APPLICATION NO. : 10/545388
DATED : June 19, 2007
INVENTOR(S) : Shibasaki et al.

It is certified that error appears in the above-identified patent and that said Letters Patent is hereby corrected as shown below:

On the title page at Column 1, line 2, in the Title after "INSTRUMENT", please insert -- , --.

Assignee information Title page (73) should read as follows:
    Akebono Brake Industry Co., Ltd.
        Tokyo, Japan
   Ryosuke Shibasaki
        Tokyo, Japan At Column 1, line 2, in the Title after "INSTRUMENT", please insert -- , --.

At Column 11, line 12 (Approx), please delete "calibrates." and insert -- calibrated. --, therefor.

At Column 11, line 28 (Approx), please delete "R ((" and insert -- R ( --, therefor.

At Column 11, line 31 (Approx) below "follows.", please insert
-- $R(\alpha, \beta, \gamma) = R_\gamma \cdot R_\beta \cdot R_\alpha$ --.

At Column 11, line 44 (Approx) after "0, -1)", please insert -- . --.

At Column 12, line 49 (Approx) after "t=0", please delete ";" and insert -- . --, therefor.

At Column 14, line 41 after "$\gamma_0$)", please insert -- . --.

At Column 16, line 20, please delete "<Connecting" and insert -- <Correcting --, therefor.

Signed and Sealed this

Sixth Day of May, 2008

JON W. DUDAS
*Director of the United States Patent and Trademark Office*